(12) United States Patent
Lowe, III

(10) Patent No.: US 6,235,750 B1
(45) Date of Patent: May 22, 2001

(54) 6-PHENYLPYRIDYL-2-AMINE DERIVATIVES USEFUL AS NOS INHIBITORS

(75) Inventor: John A. Lowe, III, Stonington, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/325,480

(22) Filed: Jun. 3, 1999

Related U.S. Application Data

(63) Continuation-in-part of application No. PCT/IB97/01446, filed on Nov. 17, 1997
(60) Provisional application No. 60/032,793, filed on Dec. 6, 1996.

(51) Int. Cl.[7] .................... C07D 213/73; C07D 401/10; C07D 413/14; A61K 31/44
(52) U.S. Cl. .................... 514/299; 514/318; 514/332; 514/307; 546/194; 546/264; 546/148; 546/183
(58) Field of Search .................... 546/194, 264, 546/148, 183; 514/318, 332, 307, 299

(56) References Cited

U.S. PATENT DOCUMENTS 5,621,004  4/1997  Dunn et al. .................... 514/551

FOREIGN PATENT DOCUMENTS

| WO9214780A | 9/1992 | (WO) . |
| WO9414780A | 4/1994 | (WO) . |
| WO9618616A | 6/1996 | (WO) . |
| WO9736871A | 10/1997 | (WO) . |
| WO9966918 | 12/1999 | (WO) . |

OTHER PUBLICATIONS

Hobbs et al. Inhibition of nitric oxide synthase as a potential therapeutic target. Annu. Rev. Pharmcol. Toxicol. 39: 191–220, 1999.*

Schmidt, Harald H. H., et al., Purification of a soluble isoform of guanylyl cyclase–activating–factor synthase, Proc. Natl. Acad. Sci USA, vol. 88, pp. 365–369, Jan. 1991.

Pollock, Jennifer S., et al. Purification and characterization of particulate endothelium–derived relaxing factor synthase from cultured and native bovine aortic endothelial cells, Proc. Natl. Acad. Sci. USA, vol. 88, pp. 10480–10484, Dec. 1991.

Bredt, David S. and Snyder, Solomon H., Isolation of nitric oxide synthetase, a colmodulin–requiring enzyme, Proc. Natl. Acad. Sci. USA, vol. 87, pp. 682–685, Jan. 1990.

Herman, Barbara H., et al., The Effects of NMDA Receptor Antagonists and Nitric Oxide Synthase Inhibitors on Opioid Tolerance and Withdrawal Medication Development Issues for Opiate Addiction, Neuropsychopharmacology, vol. 13, pp. 269–293, 1995.

Connor, Jane R., et al., Suppression of adjuvant–induced arthritis by selective inhibition of inducible nitric oxide synthase, European Journal of Pharmacology, 273, pp.15–24, 1995.

Yoshida, Tazuka, et al., The NOS Inhibitor, 7–Nitroindazole, Decreased Focal Infarct Volume but not the Response to Topical Acetylcholine in Pial Vessels, Journal of Cerebral Blood Flow and Metabolism, 14, pp. 924–929, 1994.

Garvey, Edward P., et al., Potent and Selective Inhibition of Human Nitric Oxide Synthases, The Journal of Biological Chemistry, vol. 269, No. 43, pp. 26669–26676, Oct. 28, 1994.

Iadecola,Costantino, et al., Inhibition of inducible nitric oxide synthase ameliorates cerebral ischemic damage, the American Physiological Society, pp. 286–292, 1995.

Lowe, John A. III, et al., A New Class of Selective and Potent Inhibitors of Neuronal Nitric Oxide Synthase, Bioorganic & Medicinal Chemistry, 9, pp. 2569–2572, 1999.

Moore, P.K. Characterization of the Novel Nitric Oxide Synthase Inhibitor 7–nitro Indazole and Related Indazoles: Antinociceptive and Cardiovascular Effects, Br. J. Pharmacol. (1993), 110, 219–224.

Dawson, Valina L. and Dawson, Ted M., Nitric Oxide in nerodegeneration, Progress in Brain Research, vol. 118, pp. 215–229.

Faletti, et al., Activity of Ovarian Nitric Oxide Synthase (Nos) during Ovulatory Process in the Rat: Relationship with Prostaglandins (PGs) Production, Nitric Oxide: Biology and Chemistry, vol. 3, No. 4, pp. 340–347 (1999).

Karatinos, et al., The Nitric Oxide Pathway: Potential Implications for Treatment of Neuropsychiatric Disorders, Clinical Neuropharmacology, vol. 18, No. 6, pp. 482–499.

* cited by examiner

Primary Examiner—Richard L. Raymond
Assistant Examiner—Hong Liu
(74) Attorney, Agent, or Firm—Peter C. Richardson; Paul H. Ginsburg; Kristina L. Konstas

(57) ABSTRACT

The present invention relates to 6-phenyl-pyridin-2-ylamine derivatives of the formula (I)

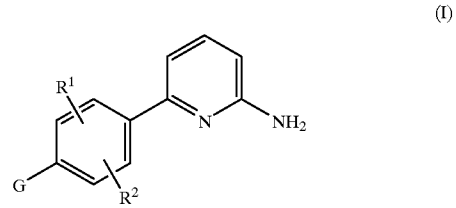

wherein G, $R^1$ and $R^2$ are defined as in the specification, that exhibit activity as nitric oxide synthase (NOS) inhibitors, to pharmaceutical compositions containing them, and to their use in the treatment and prevention of central nervous system and other disorders.

9 Claims, No Drawings

6-PHENYLPYRIDYL-2-AMINE DERIVATIVES USEFUL AS NOS INHIBITORS

This application is a continuation-in-part of PCT/IB97/01446, International Filing Date Nov. 12, 1997, designating the United States and claiming priority of U.S. Provisional Patent Application Ser. No. 60/032,793, filed Dec. 6, 1996.

The present invention relates to certain 6-phenylpyridyl-2-amine derivatives that exhibit activity as nitric oxide synthase (NOS) inhibitors, to pharmaceutical compositions containing them and to their use in the treatment and prevention of central nervous system disorders, inflammatory disorders, septic shock and other disorders.

There are three known isoforms of NOS—an inducible form (I-NOS) and two constitutive forms referred to as, respectively, neuronal NOS (N-NOS) and endothelial NOS (E-NOS). Each of these enzymes carries out the conversion of arginine to citrulline while producing a molecule of nitric oxide (NO) in response to various stimuli. It is believed that excess nitric oxide (NO) production by NOS plays a role in the pathology of a number of disorders and conditions in mammals. For example, NO produced by I-NOS is thought to play a role in diseases that involve systemic hypotension such as toxic shock and therapy with certain cytokines. It has been shown that cancer patients treated with cytokines such as interleukin 1 (IL-1), interleukin 2 (IL-2) or tumor necrosis factor (TNF) suffer cytokine-induced shock and hypotension due to NO produced from macrophages, i.e., inducible NOS (I-NOS), see *Chemical & Engineering News*, Dec. 20, p.33, (1993). I-NOS inhibitors can reverse this. It is also believed that I-NOS plays a role in the pathology of diseases of the central nervous system such as ischemia. For example, inhibition of I-NOS has been shown to ameliorate cerebral ischemic damage in rats, see *Am. J. Physiol.,* 268, p. R286 (1995)). Suppression of adjuvant induced arthritis by selective inhibition of I-NOS is reported in *Eur. J. Pharmacol.,* 273, p. 15–24 (1995).

NO produced by N-NOS is thought to play a role in diseases such as cerebral ischemia, pain, and opiate tolerance. For example, inhibition of N-NOS decreases infarct volume after proximal middle cerebral artery occlusion in the rat, see *J. Cerebr. Blood Flow Metab.,* 14, p. 924–929 (1994). N-NOS inhibition has also been shown to be effective in antinociception, as evidenced by activity in the late phase of the formalin-induced hindpaw licking and acetic acid-induced abdominal constriction assays, see *Br. J. Pharmacol.,* 110, p. 219–224 (1993). Finally, opioid withdrawal in rodents has been reported to be reduced by N-NOS inhibition, see *Neuropsychopharmacol.,* 13, p. 269–293 (1995).

SUMMARY OF THE INVENTION

The present invention relates to a compound of the formula

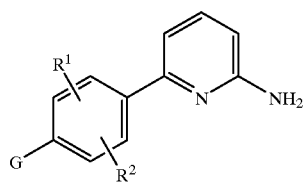

(I)

wherein $R^1$ and $R^2$ are selected, independently, from hydrogen, hydroxy, methyl and methoxy;

G is selected from [2.2.1]bicyclohept-6-ylmethyl substituted by $NR^3R^4$; [2.2.1]bicyclohept-1-ylmethyl substituted by $NR^3R^4$; 3-azabicyclo[3.2.1]octan-8-ol, 3N-substituted by isopropyl, benzyl, or furanylmethyl; (5-phenyl-cyclohexylmethyl) substituted by $NR^3R^4$; oxindolylmethyl or oxindolylmethylene, N-substituted by methyl or 2-dimethylaminoethyl; and a group of the formula

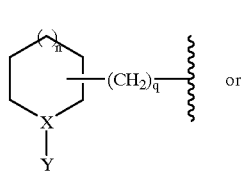

(A)

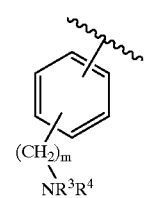

(B)

wherein n is zero or one;

Y is hydrogen, $NR^3R^4$, $(C_1-C_6)$alkyl or aralkyl, wherein the aryl moiety of said aralkyl is phenyl, naphthyl, isoxazolyl, methylenedioxybenzyl, imidazolyl, pyridyl, furyl, thiazolyl, or isothiazolyl, and the alkyl moiety is straight or branched and contains from 1 to 6 carbon atoms, and wherein said $(C_1-C_6)$alkyl and the aryl moiety of said aralkyl may be substituted with from one to three substituents, preferably from zero to two substituents, that are selected, independently, from phenyl, —C(O)NH$_2$, —C(O)phenyl, halo (e,g., chloro, fluoro, bromo or iodo), nitro, hydroxy, cyano, amino, $(C_1-C_4)$alkoxy and $(C_1-C_4)$alkylamino;

X is N when Y is hydrogen, $(C_1-C_6)$ alkyl, aralkyl, or substituted $(C_1-C_6)$alkyl, and X is CH when Y is $NR^3R^4$;

q is zero, one or two;

m is zero, one or two; and $R^3$ and $R^4$ are selected, independently, from hydrogen, $(C_1-C_6)$alkyl, —C(O)$(C_1-C_6)$alkyl, cyclohexyl, tetrahydronaphthalene and aralkyl, wherein the aryl moiety of said aralkyl is phenyl or naphthyl and the alkyl moiety is straight or branched and contains from 1 to 6 carbon atoms, and wherein said $(C_1-C_6)$alkyl or —C(O)$(C_1-C_6)$alkyl and said tetrahydronaphthalene and the aryl moiety of said aralkyl may optionally be substituted with from one to three substituents, preferably from zero to two substituents, that are selected, independently, from phenyl, halo (e.g., chloro, fluoro, bromo or iodo), nitro, hydroxy, cyano, amino, $(C_1-C_4)$ alkoxy, and $(C_1-C_4)$ alkylamino;

or $R^3$ and $R^4$ form, together with the nitrogen to which they are attached, a piperazine, piperidine or pyrrolidine ring or an azabicyclic ring containing from 6 to 14 ring members, from 1 to 3 of which are nitrogen and the rest of which are carbon;

and wherein said piperazine, piperidine, pyrrolidine and azabicyclic rings formed by $R^3$ and $R^4$ may optionally be substituted with one or more substituents, preferably with from zero to two substituents, that are selected, independently, from $(C_1-C_6)$alkyl, amino, $(C_1-C_6)$ alkylamino, [di-$(C_1-C_6)$alkyl]amino, $(C_1-C_6)$ alkylacetamido, phenyl substituted 5 to 6 membered heterocyclic rings containing from 1 to 4 rings nitrogen atoms, benzoyl, benzoylmethyl, benzylcarbonyl, phenylaminocarbonyl, phenylethyl and phenoxycarbonyl, and wherein the phenyl moieties of any of the foregoing substituents may optionally be substituted with one or more substituents, preferably with from zero to two substituents, that are selected, independently, from halo, $(C_1-C_3)$alkyl, $(C_1-C_3)$ alkoxy, nitro, amino, cyano, $CF_3$ and $OCF_3$; or a pharmaceutically acceptable salt of such compound.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1-methylene-bis-(2-hydroxy-3-naphthoate)] salts.

The term "alkyl", as used herein, unless otherwise indicated, includes saturated monovalent hydrocarbon radicals having straight, branched or cyclic moieties or combinations thereof.

The term "one or more substituents", as used herein, refers to a number of substituents that equals from one to the maximum number of substituents possible based on the number of available bonding sites.

The term "halo", as used herein, unless otherwise indicated, includes chloro, fluoro, bromo and iodo.

In one embodiment, the present invention relates to a compound of formula I as escribed above, wherein G is a group of the formula

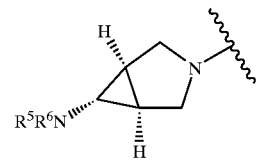

(A)

(B)

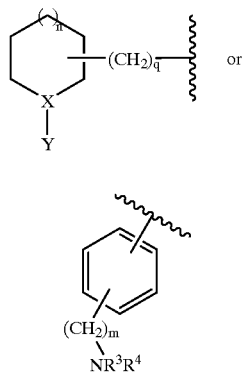

wherein n is zero or one;

Y is $NR^3R^4$, $(C_1-C_6)$alkyl or aralkyl, wherein the aryl moiety of said aralkyl is phenyl or naphthyl and the alkyl moiety is straight or branched and contains from 1 to 6 carbon atoms, and wherein said $(C_1-C_6)$alkyl and the aryl moiety of said aralkyl may be substituted with from one to three substituents, preferably from zero to two substituents, that are selected, independently, from halo (e.g., chloro, fluoro, bromo or iodo), nitro, hydroxy, cyano, amino, $(C_1-C_4)$alkoxy and $(C_1-C_4)$ alkylamino;

X is N when Y is $(C_1-C_6)$ alkyl, aralkyl, or substituted $(C_1-C_6)$alkyl, and X is CH when Y is $NR^3R^4$;

q is zero, one or two;

m is zero, one or two; and $R^3$ and $R^4$ are selected, independently, from $(C_1-C_6)$ alkyl, tetrahydronaphthalene and aralkyl, wherein the aryl moiety of said aralkyl is phenyl or naphthyl and the alkyl moiety is straight or branched and contains from 1 to 6 carbon atoms, and wherein said $(C_1-C_6)$ alkyl and said tetrahydronaphthalene and the aryl moiety of said aralkyl may optionally be substituted with from one to three substituents, preferably from zero to two substituents, that are selected, independently, from halo (e.g., chloro, fluoro, bromo or iodo), nitro, hydroxy, cyano, amino, $(C_1-C_4)$ alkoxy, and $(C_1-C_4)$ alkylamino;

or $R^3$ and $R^4$ form, together with the nitrogen to which they are attached, a piperazine, piperidine or pyrrolidine ring or an azabicyclic ring containing from 6 to 14 ring members, from 1 to 3 of which are nitrogen and the rest of which are carbon;

or a pharmaceutically acceptable salt of such compound.

Examples of preferred compounds of this invention are compounds of the formula I, and their pharmaceutically acceptable salts, wherein $NR^3R^4$ is:

4-phenylethylpiperazin-1-yl;

4-methylpiperazin-1-yl;

phenethylamino; or 3-aza-bicyclo[3.1.0]hex-6-ylamine.

Other preferred compounds of this invention are compounds of the formula I, and their pharmaceutically acceptable salts, wherein $NR^3R^4$ is a group of the formula wherein $NR^5R^6$ is $NH_2$.

Other preferred compounds of this invention are compounds of the formula I wherein G is a group of the formula A, X is nitrogen and q is zero.

Other embodiments of this invention relate to compounds of the formula I wherein q is zero or one.

Other embodiments of the invention relate to compounds of the formula I wherein G is a group of the formula B and $NR^3R^4$ does not form a cyclic moiety.

Other embodiments of this invention relate to compounds of the formula I wherein G is a group of the formula B, m is two and $NR^3R^4$ does not form a cyclic moiety (i.e., where N, $R^3$ and $R^4$ are part of the same ring structure).

Other embodiments of this invention relate to compounds of the formula I wherein G is a group of the formula B, m is one and $NR^3R^4$ does not form a cyclic moiety.

Other embodiments of this invention relate to compounds of the formula I wherein G is a group of the formula B, m is zero and $NR^3R^4$ does not form a cyclic moiety.

Other embodiments of the invention relate to compounds of the formula I wherein G is a group of the formula B and m is zero.

Other embodiments of this invention relate to compounds of the formula I wherein G is a group of the formula A and both p and n are one.

Other embodiments of this invention relate to compounds of the formula I wherein G is a group of the formula A, p is one, q is zero and n is one.

Other embodiments of this invention relate to compounds of the formula I wherein G is a group of the formula B and m is one.

Other embodiments of this invention relate to compounds of the formula I wherein G is a group of the formula A and p is one.

The present invention also relates to a pharmaceutical composition for treating or preventing a condition selected from the group consisting of migraine, inflammatory diseases (e.g., asthma), stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addiction (e.g., dependencies on drugs, alcohol and nicotine), emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, Parkinson's disease, glaucoma, macular degeneration, diabetic neuropathy, diabetic nephropathy and cancer in a mammal, including a human, comprising an amount of a compound of the formula I, or a pharmaceutically acceptable salt thereof that is effective in treating or preventing such condition, and a pharmaceutically acceptable carrier.

The present invention also relates to a pharmaceutical composition for treating or preventing depression in a mammal, including a human, comprising an amount of a compound of the formula I, and a pharmaceutically acceptable carrier.

The present invention also relates to a method of treating or preventing a condition selected from the group consisting of migraine, inflammatory diseases (e.g., asthma), stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addictions (e.g., dependencies on drugs, alcohol and nicotine), emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, Parkinson's disease, glaucoma, macular degeneration, diabetic neuropathy, diabetic nephropathy and cancer in a mammal, including a human, comprising administering to said mammal an amount of a compound of the formula I, or a pharmaceutically acceptable salt thereof, that is effective in treating or preventing such condition.

The present invention also relates to a method of treating or preventing depression in a mammal, including a human, comprising administering to said mammal an amount of a compound of the formula I, or a pharmaceutically acceptable salt thereof, that is effective in treating or preventing depression.

The present invention also relates to a pharmaceutical composition for inhibiting nitric oxide synthase (NOS) in a mammal, including a human, comprising an NOS inhibiting effective amount of a compound of the formula I, or a pharmaceutically acceptable salt thereof and a pharmaceutically acceptable carrier.

The present invention also relates to a method of inhibiting NOS in a mammal, including a human, comprising administering to said mammal a NOS inhibiting effective amount of a compound of the formula I, or a pharmaceutically acceptable salt thereof.

The present invention also relates to a pharmaceutical composition for treating or preventing a condition selected from the group consisting of migraine, inflammatory diseases (e.g., asthma), stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addictions (e.g., dependencies on drugs, alcohol and nicotine), emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, glaucoma, macular degeneration, diabetic neuropathy, diabetic nephropathy and cancer in a mammal, including a human, comprising a NOS inhibiting effective amount of a compound of the formula I, or a pharmaceutically acceptable salt thereof and a pharmaceutically acceptable carrier.

The present invention also relates to a pharmaceutical composition for treating or preventing depression in a mammal, including a human, comprising a NOS inhibiting effective amount of a compound of the formula I, or a pharmaceutically acceptable salt thereof, and a pharmaceutically acceptable carrier.

The present invention also relates to a method of treating or preventing a condition selected from the group consisting of migraine, inflammatory diseases (e.g., asthma), stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addictions (e.g., dependencies on drugs, alcohol or nicotine), emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, Parkinson's disease, glaucoma, macular degeneration, diabetic neuropathy, diabetic nephropathy and cancer in a mammal, including a human, comprising administering to said mammal a NOS inhibiting effective amount of a compound of the formula I, or a pharmaceutically acceptable salt thereof.

The present invention also relates to a method of treating or preventing depression in a mammal, including a human, comprising administering to said mammal a NOS inhibiting effective amount of a compound of the formula I, or a pharmaceutically acceptable salt thereof.

Compounds of formula I have chiral centers and therefore may exist in different enantiomeric and diastereomeric forms. This invention relates to all optical isomers and all stereoisomers of compounds of the formula I and mixtures thereof, and to all pharmaceutical compositions and methods of treatment defined above that contain or employ them, respectively.

Formula I above includes compounds identical to those depicted but for the fact that one or more hydrogen, carbon or other atoms are replaced by isotopes thereof. Such compounds may be useful as research and diagnostic tools in metabolism pharmacokinetic studies and in binding assays.

DETAILED DESCRIPTION OF THE INVENTION
The compounds of the formula I may be prepared as described in the following reaction schemes and discussion. Unless otherwise indicated, $R^1$, $R^2$, $R^3$, $R^4$, $R^5$, $R^6$, $R^7$, $R^8$ and $R^9$ and structural formula I in the reaction schemes and discussion that follow are defined as above.
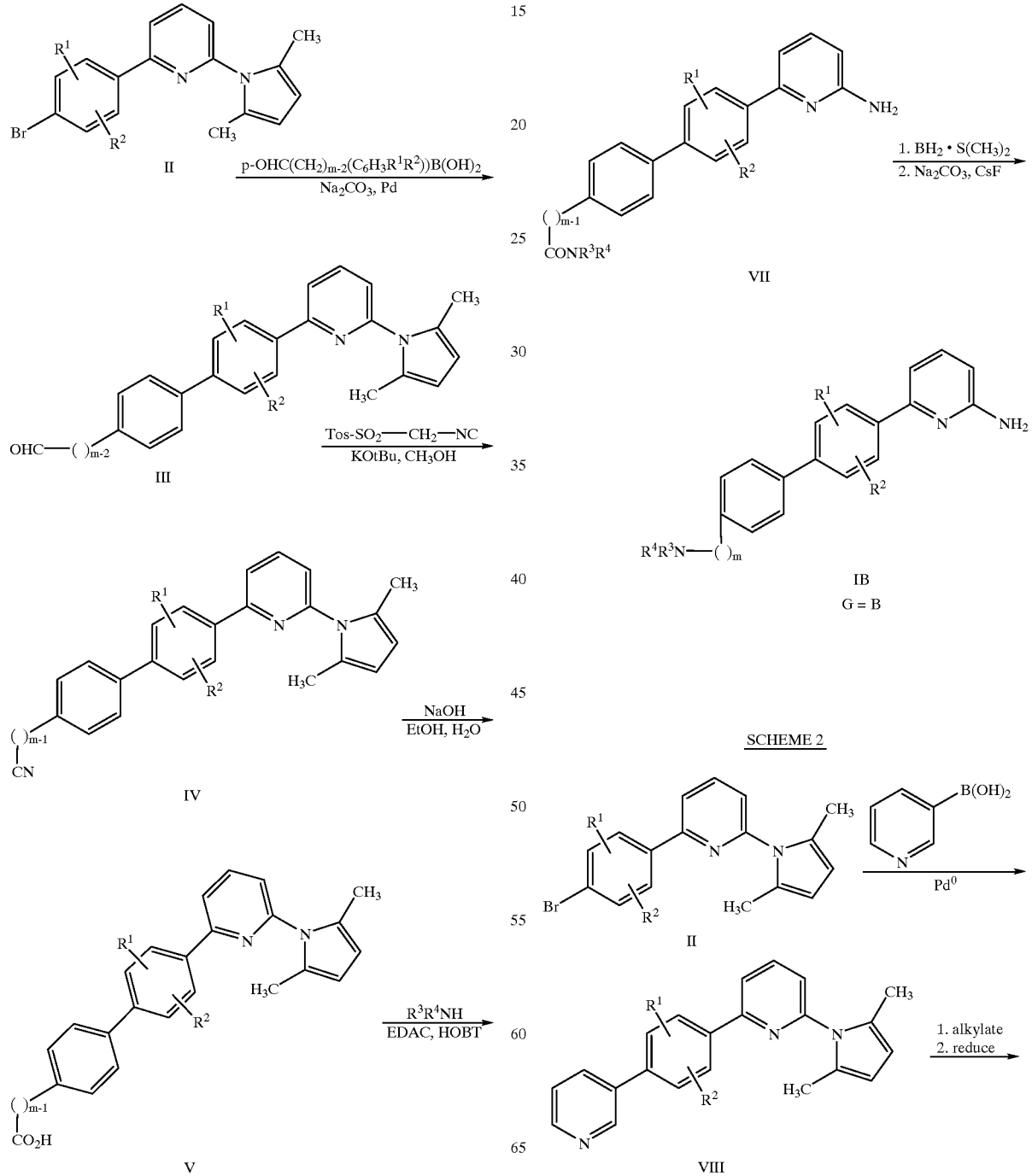

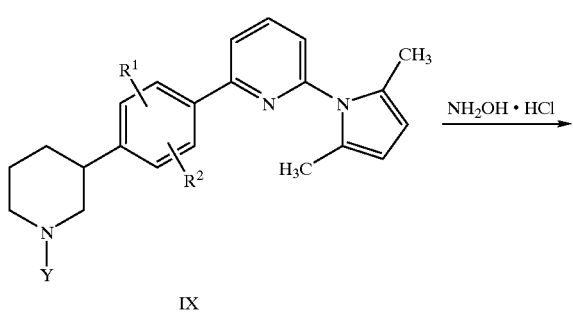
IX
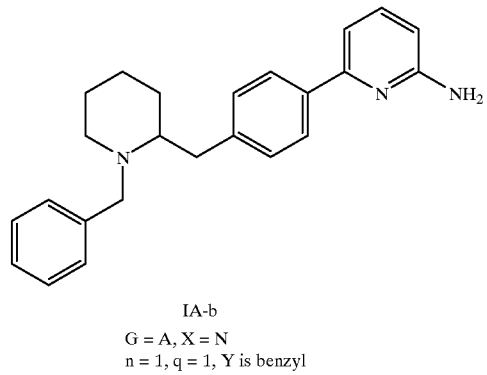
IA-b
G = A, X = N
n = 1, q = 1, Y is benzyl
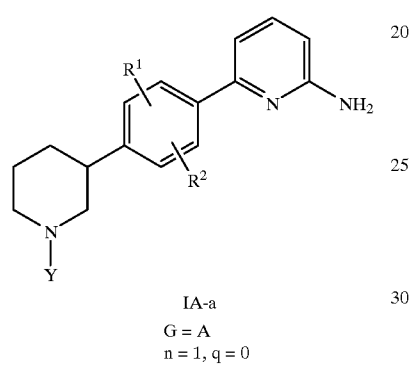
IA-a
G = A
n = 1, q = 0
SCHEME 4
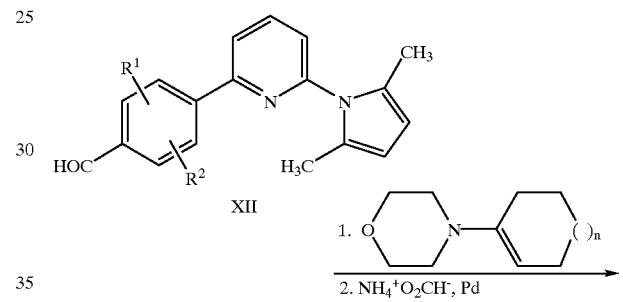
XII
SCHEME 3
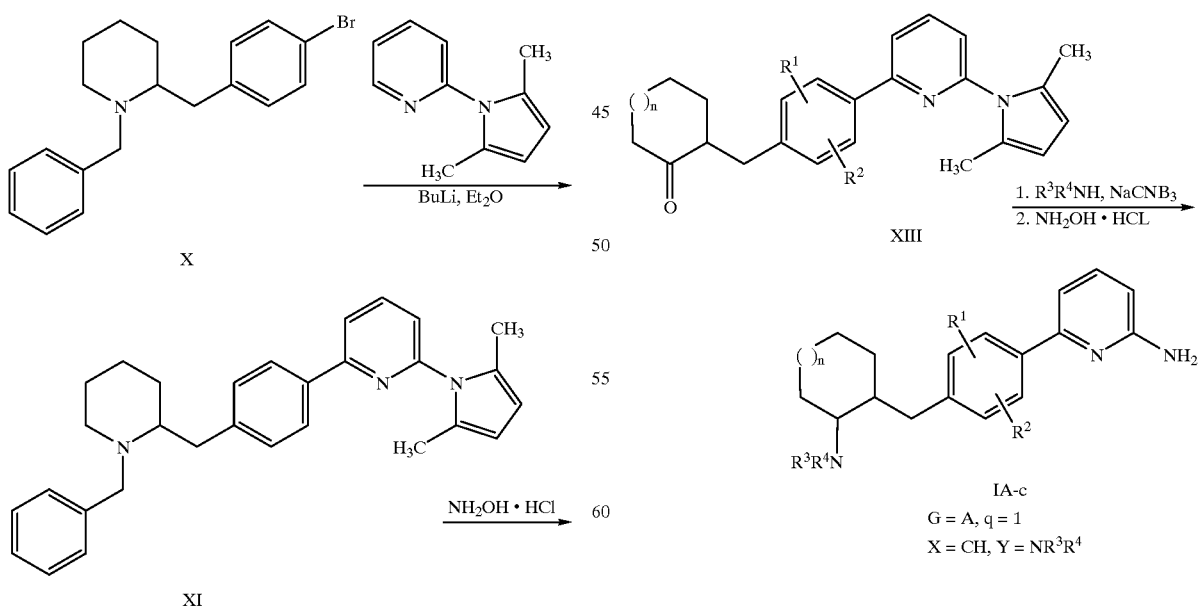

SCHEME 5

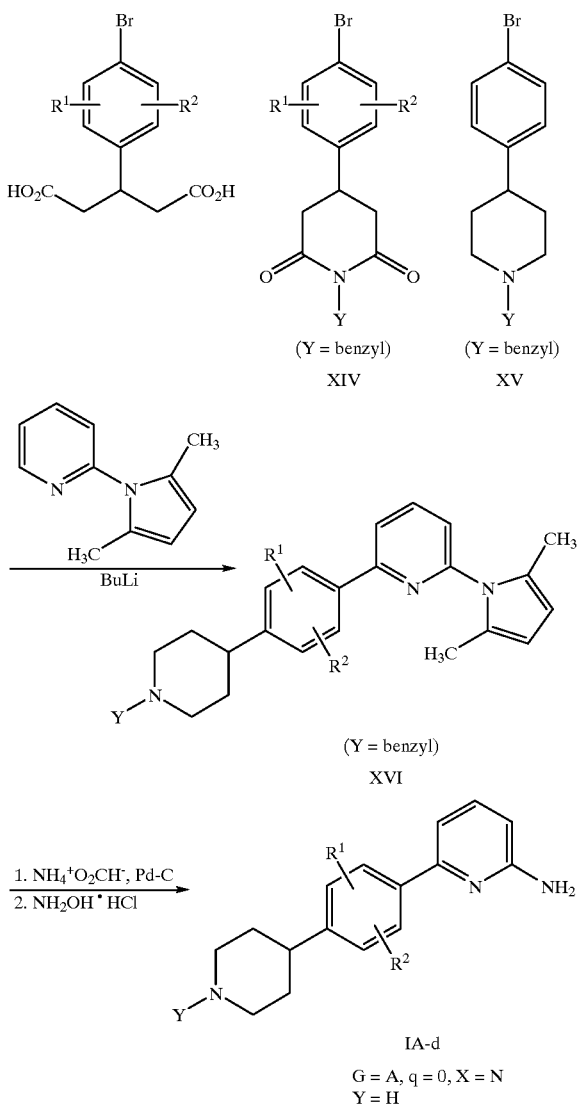

G = A, q = 0, X = N
Y = H

The starting materials used in the procedures of Schemes 1–5 are either commercially available, known in the art or readily obtainable from known compounds using methods that will be apparent to those skilled in the art.

Referring to Scheme 1, compound II is prepared by reaction of 1,4-dibromobenzene with an organolithium reagent, preferably butyl lithium, at a temperature from −100° C. to about 0° C., followed by addition to 2-(2,5-dimethylpyrrolyl)-pyridine at a temperature from about about 0° C. to about 50° C. in an ethereal solvent, preferably diethyl ether, for about 1 to 24 hours. Compound III is prepared by reacting II with a boronic acid derivative of the formula p-OHC(CH$_2$)$_{m-2}$(C$_6$H$_3$R$^1$R$^2$)B(OH)$_2$ in a solvent consisting of an alcohol, preferably ethanol, optionally mixed with water and a halogenated hydrocarbon, at a temperature from about 25° C. to about 150° C., for about 1 to 24 hours, using a palladium-based catalyst, either palladium-zero or palladium-two oxidation state, typically with phosphine ligands, preferably tetrakistriphenylphosphine palladium.

Compound IV is prepared by reacting III with tosylmethylisocyanide in the presence of potassium t-butoxide and ethanol, in an ethereal solvent such as 1,2-dimethoxyethane, at a temperature from about −100° C. to about 100° C., for about 1 to 24 hours. Compound V is prepared from IV by basic hydrolysis of the nitrile using an alkali metal hydroxide in an aqueous alcohol-based solvent, such as aqueous ethanol, at a temperature from about 25° C. to about 125° C., for about 30 minutes to 48 hours. Compound VI is prepared from V by dehydrative coupling with ammonia, a primary or secondary amine of the formula R$^3$R$^4$NH effected by a dehydrating agent such as a carbodiimide, for example, N-ethyl-N-(dimethylaminopropyl)-carbodiimide, in a solvent that is a halogenated hydrocarbon or a N,N-dialkylamide, such as dimethylformamide, at a temperature from about 0° C. to about 100° C., for about 1 to 48 hours. Compound VII is prepared from VI by deblocking using hydroxylamine hydrochloride in an aqueous or alcoholic solvent, preferably aqueous ethanol, at a temperature from about 25° C. to about 100° C., for about 1 to 48 hours, and may include deblocking a protecting group such a the t-butoxycarbonyl group by reaction with trifluoroacetic acid or a related polyhalogenated acetic acid or a gaseous hydrogen halide such as HCl, in a halogenated hydrocarbon, ethereal solvent or ethyl acetate, at a temperature from about −70° C. to about 100° C., for about 10 minutes to 24 hours.

The final compound in Scheme 1, IB, wherein G=B, is prepared by reduction of VII with borane, a trialkyl borane, alane, or lithium aluminum hydride in an ethereal solvent, such as ethyl ether or tetrahydrofuran, at a temperature from about −100° C. to about 100° C., for about 30 minutes to 24 hours, and optionally using cesium fluoride and an alkali metal or alkaline earth carbonate in an aqueous alcoholic solvent, at a temperature from about 25° C. to about 125° C. for 1 to 72 hours.

Referring to Scheme 2, compound VIII is prepared from II by reaction with 3-pyridyl boronic acid and a palladium catalyst, in either the palladium-zero or palladium-two oxidation state, with ligands typically comprised of trialkyl or triaryl phosphines, such as tetrakistriphenylphosphine palladium, in an aqueous alcoholic solvent at a temperature from about 25° C. to about 125° C. for about 1 to 48 hours. Compound IX is prepared from VIII by alkylation with an alkyl or aralkyl halide or sulfonate, in an ethereal, alcoholic, aqueous alcoholic, or dialkylamine-based solvent, such as dimethylformamide, at a temperature from about 0° C. to about 125° C. for about 30 minutes to 72 hours, followed by reduction with a borohydride- or aluminum hydride-based reagent, such as sodium borohydride, in an ethereal, alcoholic, or aqueous-alcoholic solvent, typically methanol, at a temperature from about 0° C. to about 125° C. for about 1 to 72 hours. The final compound in Scheme 2, compound IA-a, where G=A, n=1, and q=0, is prepared from IX by deblocking with hydroxylamine hydrochloride in an alcoholic or aqueous-alcoholic solvent, typically aqueous ethanol, at a temperature from about 25° C. to about 125° C. for about 1 to 72 hours.

In the process of Scheme 2, the preferred value of Y in formulas IX and IA-a is benzyl. Compounds of the formula IA-a wherein Y is benzyl can be converted into the corresponding compounds wherein Y is other than benzyl by debenzylation using hydrogen or ammonium formate in the presence of a noble metal catalyst, such as palladium, in an ethereal, halogenated hydrocarbon, alcoholic, or aqueous alcoholic solvent, at a temperature from 0° C. to 100° C. for a time from 30 minutes to 24 hours, followed by reductive amination with with an alkyl or aralkyl aldehyde in the presence of a borohydride-based reagent such as sodium cyanoborohydride or sodium triacetoxyborohydride, in an ethereal, halogenated hydrocarbon, alcoholic, or aqueous-alcoholic solvent, at a temperature from 0° C. to 100° C. for a time from 1 to 72 hours.

Referring to Scheme 3, compound X is prepared by reductive amination of 2-(4-bromophenylmethyl)-piperidine with benzaldehyde and a borohydride-based reagent such as sodium cyanoborohydride or sodium triacetoxyborohydride, in an ethereal, halogenated hydrocarbon, alcoholic, or aqueous-alcoholic solvent, at a temperature from about 0° C. to about 100° C. for about 1 to 72 hours. Compound XI is prepared from compound X by reaction of compound X with an organolithium reagent, typically butyl lithium, followed by addition of the resulting organolithium reagent to 2-(2,5-dimethylpyrrolyl)-pyridine, in an ethereal solvent such as ethyl ether, at a temperature from about −70° C. to about 100° C. for about 30 minutes to 48 hours. The final compound in Scheme 3, IA-b, wherein G=A, n=1, q=1 and Y is benzyl, is prepared from compound XI by deblocking with hydroxylamine hydrochloride in an alcoholic or aqueous-alcoholic solvent, typically aqueous ethanol, at a temperature from about 25° C. to about 125° C. for about 1 to 72 hours.

Compounds of the formula IA-b can be converted into the corresponding compounds wherein Y is other than benzyl using the procedure described above for converting compounds of the formula IA-a into the analogous compounds wherein Y is other than benzyl.

Referring to Scheme 4, compound XII is prepared from 6-bromo-2-(2,5-dimethylpyrrolyl)-pyridine and 4-formylphenylboronic acid in the presence of a palladium catalyst, in either the palladium-zero or palladium-two oxidation state, with ligands typically comprised of trialkyl or triaryl phosphines, such as tetrakis-triphenylphosphine palladium, in an aqueous alcoholic solvent, at a temperature from about 25° C. to about 125° C. for about 1 to 48 hours. Compound XIII is then prepared from XII by reaction of XII with the enamine of a ketone or aldehyde, typically the morpholine or pyrrolidine enamine, in a aromatic hydrocarbon, hydrocarbon, or halogenated hydrocarbon solvent, preferably toluene, at a temperature from about 25° C. to about 150° C. for about 1 to 72 hours, followed by an aqueous hydrolysis step, typically with aqueous hydrochloric acid, and then reduction with hydrogen or ammonium formate in the presence of a noble metal catalyst, such as palladium, in an ethereal, halogenated hydrocarbon, alcoholic, or aqueous alcoholic solvent, at a temperature from about 0° C. to about 100° C. for about 30 minutes to 24 hours. The final compound in Scheme 4, IA, where G=A, q=1, X=CH, and Y=NR$^3$R$^4$, is prepared by reductive amination of compound XIII with ammonia, a primary amine, or a secondary amine in the presence of a borohydride-based reagent such as sodium cyanoborohydride or sodium triacetoxyborohydride, in an ethereal, halogenated hydrocarbon, alcoholic, or aqueous-alcoholic solvent, at a temperature from about 0° C. to about 100° C. for about 1 to 72 hours, followed by deblocking with hydroxylamine hydrochloride in an alcoholic or aqueous-alcoholic solvent, typically aqueous ethanol, at a temperature from about 25° C. to about 125° C. for about 1 to 72 hours.

Referring to Scheme 5, compound XIV is prepared from 3-(4-bromophenyl)-glutaric acid by dehydration with acetic anhydride or a similar dehydrating reagent, followed by reaction with benzylamine in a hydrocarbon, aromatic hydrocarbon, or halogenated hydrocarbon solvent, at a temperature from about 25° C. to about 180° C for about 1 to 48 hours, followed by dehydration with acetic anhydride, or a similar dehydrating reagent, at a temperature from about 25° C. to about reflux for about 1 to 48 hours. Compound XV is prepared by reduction of XIV with borane, borane methyl sulfide, alane, or lithium aluminum hydride in an ethereal or hydrocarbon solvent, at a temperature from about 0° C. to about 100° C. for about 30 minutes to 48 hours. Compound XVI is prepared from compound XV by reaction of compound XV with an organolithium reagent, typically butyl lithium, followed by addition of the resulting organolithium reagent to 2-(2,5-dimethylpyrrolyl)-pyridine, in an ethereal solvent, such as ethyl ether, at a temperature from about −70° C. to about 100° C. for about 30 minutes to 48 hours. The final compound in Scheme 5, IA-d, where G=A, Y=H, q=0, and X=N, is prepared by debenzylation of compound XVI using hydrogen or ammonium formate in the presence of a noble metal catalyst, such as palladium, in an ethereal, halogenated hydrocarbon, alcoholic, or aqueous alcoholic solvent, at a temperature from 0° C. to 100° C. for a time from 30 minutes to 24 hours, followed by deblocking with hydroxylamine hydrochloride in an alcoholic or aqueous-alcoholic solvent, typically aqueous ethanol, at a temperature from about 25° C. to about 125° C. for about 1 to 72 hours.

Compounds of the formula IA-d, which are prepared using the procedures of Scheme 5, can be converted into the analogous compounds wherein Y is alkyl or aralkyl, by reductive amination with an alkyl or aralkyl aldehyde in the presence of a borohydride-based reagent such as sodium cyanoborohydride or sodium triacetoxyborohydride, in an ethereal, halogenated hydrocarbon, alcoholic, or aqueous-alcoholic solvent, at a temperature from 0° C. to 100° C. for a time from 1 to 72 hours.

The preparation of other compounds of the formula I not specifically described in the foregoing experimental section can be accomplished using combinations of the reactions described above that will be apparent to those skilled in the art.

In each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred as a matter of convenience.

The compounds of formulae I ("the active compounds of this invention") which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the active base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The active compounds of this invention and their pharmaceutically acceptable salts are useful as NOS inhibitors i.e., they possess the ability to inhibit the NOS enzyme in mammals, and therefore they are able to function as therapeutic agents in the treatment of the aforementioned disorders and diseases in an afflicted mammal.

The active compounds of this invention and their pharmaceutically acceptable salts can be administered via either the oral, parenteral or topical routes. In general, these compounds are most desirably administered in dosages ranging from about 0.01 to about 250 mg per day, in single or divided doses (i.e., from 1 to 4 doses per day), although variations will necessarily occur depending upon the species, weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The active compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tablefting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the active compounds of the present invention topically when treating inflammatory conditions of the skin and this may be done by way of creams, jellies, gels, pastes, patches, ointments and the like, in accordance with standard pharmaceutical practice.

The ability of compounds of the formulae I to inhibit NOS may be determined using procedures described in the literature. The ability of compounds of the formulae I to inhibit endothelial NOS may be determined by using the procedures described by Schmidt et al. in *Proc. Natl. Acad. Sci. U.S.A.,* 88, pp. 365–369 (1991) and by Pollock et al., in *Proc. Natl. Acad. Sci. U.S.A.,* 88, pp. 10480–10484 (1991). The ability of compounds of the formulae I to inhibit inducible NOS may be determined using the procedures described by Schmidt et al., in *Proc. Natl. Acad, Sci. U.S.A.,* 88 pp. 365–369 (1991) and by Garvey et al. in *J. Biol. Chem.,* 269, pp. 26669–26676 (1994). The ability of the compounds of the formulae I to inhibit neuronal NOS may be determined using the procedure described by Bredt and Snyder in *Proc. Natl. Acad. Sci. U.S.A.,* 87, 682–685 (1990).

Of 100 compounds of the formula I that were tested, all exhibited an $IC_{50}<10\,\mu M$ for inhibition of either inducible or neuronal NOS.

The present invention is illustrated by the following examples. It will be understood, however, that the invention is not limited to the specific details of these examples. Melting points are uncorrected. Proton nuclear magnetic resonance spectra ($^1H$ NMR) and $C^{13}$ nuclear magnetic resonance spectra were measured for solutions in deuterochloroform ($CDCl_3$) or in $CD_3OD$ or $CD_3SOCD_3$ and peak positions are expressed in parts per million (ppm) downfield from tetramethylsilane (TMS). The peak shapes are denoted as follows: s, singlet; d, doublet; t, triplet; q, quartet, m, multiplet, b, broad.

EXAMPLE 1

3-{2-[4'-(6-Amino-pyridin-2-yl)-biphenyl-4-yl]-ethyl}-3-aza-bicyclo[3.10.]hex-6-ylamine A. 2-(2,5-Dimethylpyrrolyl)-6-(4-bromophenyl))-pyridine To a 100 mL 3-necked round-bottomed flask equipped with septum and nitrogen ($N_2$) inlet were added 3.54 gram (g) (15 mmol) 1,4-dibromobenzene and 15 mL dry ether. The solution was cooled to $-70°$ C., and 6.25 mL (10 mmol) of a 1.6 M solution of butyl lithium in tetrahydrofuran added dropwise over 5 minutes. The reaction was stirred 5 minutes at $-70°$ C., then warmed to room temperature over 15 minutes. To the resulting solution was added a solution of 1.72 g (10 mmol) 2-(2,5-dimethylpyrrolyl)-pyridine in 5 mL ether, producing a deep red color, and the reaction stirred 3 hours at room temperature. It was then quenched with aqueous ammonium chloride solution, taken up in ethyl acetate, and washed with aqueous ammonium chloride and brine, dried over sodium sulfate, and evaporated. The residue was chromatographed on silica gel using hexane/ethyl acetate as eluant to afford 820 mg (25%) of an oil.

$^1$H-NMR (δ, $CDCl_3$): 2.30 (s, 6H), 6.03 (s, 2H), 7.20 (dd, J=1,8, 1H), 7.64 (m, 2H), 7.73 (dd, J=1,8, 1H), 7.90 (dt, J=1,8, 1H), 8.00 (m, 2H).

13C-NMR (δ, CDCl₃): 13.6, 107.2, 118.1, 120.2, 123.9, 127.0, 128.6, 132.0, 1337.3, 138.8, 151.8, 155.7.

MS (%): 327/329 (100/98, Br⁷⁹/Br⁸¹, parent+1).

B. 2-(2,5-Dimethylpyrrolyl)-6-(4-(4-formylphenyl)phenyl))-pyridine

To a 100 mL round-bottomed flask equipped with condenser and N₂ inlet were added 630 mg (1.93 mmol) 2-(2,5-dimethylpyrrolyl)-6-(4-bromophenyl)-pyridine, 289 mg (1.93 mmol) 4-formyl phenylboronic acid, 817 mg (7.71 mmol) sodium carbonate, 112 mg (0.096 mmol) tetrakistriphenylphosphine palladium, 9 mL ethanol, and 1 mL water. The mixture was heated at reflux for 14 hours, cooled, poured into water, and extracted into ethyl acetate. The organic layer was washed with brine, dried, and evaporate, and the residue chromatographed on silica gel using 25% ethyl acetate in hexane as eluant to afford 540 mg (80%) of the product.

¹H-NMR (δ CDCl₃): 2.23 (s, 6H), 5.94 (s, 2H), 7.17 (δ J=8, 1H), 7.74 (m, 2H), 780 (m, 3H), 7.90 (t, J=8, 1H), 7.96 (m, 2H), 8.19 (m, 2H), 10.05 (s, 1H).

¹³C-NMR (δ CDCl₃): 13.5, 107.1, 118.4, 120.2, 127.6, 127.7, 130.3, 138.7, 140.5, 146.4, 156.0, 191.9.

MS (%): 353 (100, parent+1).

C. 2-(2,5-Dimethylpyrrolyl)-6-(4-(4-(cyanomethyl)phenyl)phenyl))-pyridine

To a 100 mL 3N round-bottomed flask equipped with septum and N₂ inlet were added 354 mg (3.16 mmol) potassium t-butoxide and 5 mL dry 1,2-dimethoxyethane. The mixture as cooled in a −60° C. bath (CHCl₃/CO₂), and a solution of 317 mg (1.62 mmol) tosylmethylisocyanide in 5 mL dry 1,2-dimethoxyethane added dropwise. After a few minutes, a solution of 540 mg (1.53 mmol) 2-(2,5-dimethylpyrrolyl)-6-(4-(4-formylphenyl)phenyl))-pyridine in 10 mL dry 1,2-dimethoxyethane was added dropwise, and stirring continued at −60° C. for 50 minutes. Then 5 mL methanol was added and the reaction warmed and then refluxed for 15 minutes. The reaction was cooled and evaporated, and the residue taken up in water with 0.5 mL acetic acid and methylene chloride. The aqueous layer was reextracted with methylene chloride, and the combined organic layer washed with aqueous sodium bicarbonate solution, dried over sodium sulfate, and evaporated. The residue was chromatographed on silica gel using 25% ethyl acetate in hexane as eluant to afford 220 mg (40%) of the product.

¹H-NMR (δ, CDCl₃): 2.26 (s, 6H), 3.78 (s, 2H), 5.98 (s, 2H), 7.17 (δ, J=8, 1H), 7.41 (m, 2H), 7.6–7.7 (m, 4H), 7.79 (δ J=8, 1H), 7.89 (t, J=8, 1H), 8.17 (m, 2H).

¹³C-NMR (δ, CDCl₃): 13.6, 23.3, 107.1, 118.3, 120.0, 127.4, 127.5, 127.8, 128.5, 128.7, 129.3, 137.6, 138.7, 140.3, 141.0, 151.8, 156.3.

MS (%): 364 (100, parent+1).

A byproduct eluting after the product was characterized as the oxazole, 40 mg (7%):

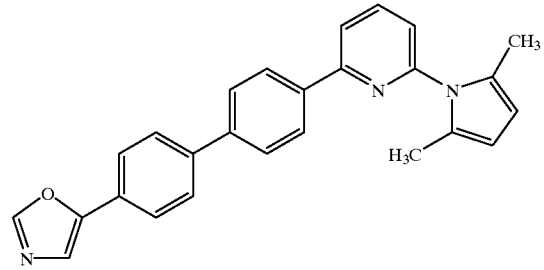

D. 2-(2,5-Dimethylpyrrolyl)-6-(4-(4-(carboxymethyl)phenyl)phenyl))-pyridine

To a 100 mL round-bottomed flask equipped with condenser and N₂ inlet were added 220 mg (0.606 mmol) 2-(2,5-dimethylpyrrolyl)-6-(4-(4-(cyanomethyl)phenyl)phenyl))-pyridine and 7 mL ethanol to form a solution at reflux. A 10% solution of sodium hydroxide in water was added slowly dropwise at reflux to maintain solution, requiring 30–60 minutes for 15 mL (and a little further ethanol). Refluxing was maintained for a total of 2.5 hours. The reaction was cooled to 0° C. and the pH adjusted with 6N hydrochloric acid to 1, and the reaction was extracted into ethyl acetate. The organic layer was washed with brine, dried over sodium sulfate, and evaporated to afford the product as an oil, used directly in the next step.

¹H-NMR (δ CDCl₃): 2.24 (s, 6H), 3.70 (s, 2H), 5.95 (s, 2H), 7.14 (δ J=8, 1H), 7.38 (m, 2H), 7.61 (m, 2H), 7.68 (m, 2H), 7.77 (δJ=8, 1H), 7.87 (t, J=8, 1H), 8.13 (m, 2H).

¹³C-NMR (δ CDCl₃): 13.5, 20.8, 107.1, 118.4, 120.2, 127.3, 127.4, 128.7, 129.9, 132.9, 137.2, 138.8, 139.5, 141.6, 151.7, 156.4.

MS (%): 383 (100, parent+1).

E. 2-(2,5-Dimethylpyrrolyl)-6-(4-(4-(6-t-butylcarboxamido-3-aza-bicyclo[3.1.0]hex-3-ylcarboxamido)methyl)phenyl)phenyl))-pyridine To a 100 mL round-bottomed flask equipped with N₂ inlet were added 420 mg (1.099 mmol)2-(2,5-dimethylpyrrolyl)-6-(4-(4-(carboxymethyl)phenyl)phenyl))-pyridine, 218 mg (1.099 mmol) 3-aza-bicyclo[3.1.0]hex-6-ylamine t-butylcarbamate, 211 mg (1.099 mmol) EDAC, 10 mg HOBT, 7 mL dry acetonitrile, and 337 uL (2.42 mmol) triethylamine. The reaction was stirred at room temperature for 20 hours evaporated, and the residue chromatographed on silica gel using 5% methanol in methylene chloride as eluant to afford the product, 280 mg (45%).

¹H-NMR (δ, CDCl₃): 1.69 (m, 2H), 2.22 (s, 6H), 3.4–3.9 (multiplets, 7H), 4.97 (bs, 1H), 5.93 (s, 2H), 7.12 (δ, J=8, 1H), 7.29 (m, 2H), 7.57 (m, 2H), 7.67 (m, 2H), 7.75 (δ, J=8, 1H). 7.85 (t, J=8, 1H), 8.12 (m, 2H).

¹³C-NMR (δ, CDCl₃): 13.5, 28.4, 42.0, 47.9, 48.8, 53.5, 79.8, 107.0 118.3, 119.9, 127.3, 127.4, 128.7, 129.5, 134.0, 137.2, 138.7, 138.9, 141.6, 151.7, 156.2, 156.4, 169.8.

MS (%): 563 (100, parent+1).

F. 2-{3-[4'-(6-amino-pyridin-2-yl)-biphenyl-4-yl]}-3-aza-bicyclo[3.1.0]hex-6-ylamine acetamide To a 100 mL round-bottomed flask equipped with condenser and N₂ inlet were added 280 mg (0.498 mmol) 2-(2,5-dimethylpyrrolyl)-6-(4-(4-(6-t-butylcarboxamido-3-aza-bicyclo[3.1.0]hex-3-ylcarboxamido)methyl)phenyl)phenyl))-pyridine, 173 mg (2.49 mmol) hydroxylamine hydrochloride, 1 mL water and 5 mL ethanol. The reaction was refluxed 40 hours, an additional 173 mg hydroxylamine hydrochloride and 5 mL ethanol added, and refluxing continued 24 hours. The reaction was cooled, poured into aqueous sodium bicarbonate solution, and extracted with a mixture of ethyl acetate and methanol, due to the limited solubility of the product in ethyl acetate. The organic layer was dried over sodium sulfate and evaporated.

The residue was taken up in 6 mL dry methylene chloride and treated with 1.5 mL triflurooacetic acid at room temperature for 1.5 hours. The reaction was evaporated, taken up in 1 N hydrochloric acid, washed with ethyl acetate, then the pH adjusted to 10 with 1 N sodium hydroxide solution, and extracted with a mixture of ethyl acetate and methanol. The organic layer was dried over sodium sulfate and evaporated to afford 160 mg (84%) of the product as a low-melting solid.

$^1$H-NMR ($\delta$, CDCl$_3$): 1.39 (bs, 2H), 1.78 (bs, 1H), 3.2–3.6 (multiplets, 2H), 3.41 (bs, 2H), 4.90 (bs, 1H), 6.30 ($\delta$, J=8, 1H), 6.83 ($\delta$, J=7.5, 1H), 7.06 (m, 2H), 7.29 (t, J=8, 1H), 7.38 (m, 2H), 7.44 (m, 2H), 7.69 (m, 2H).

$^{13}$C-NMR ($\delta$, CDCl$_3$): 25.0, 25.3, 34.9, 41.5, 107.6, 110.7, 126.8, 127.0, 127.1, 129.1, 133.2, 138.5, 129.0, 140.5, 155.3, 158.8, 170.6.

MS (%): 385 (100, parent+1).

G. 3-{2-[4'-(6-Amino-pyridin-2-yl)-biphenyl-4-yl]-ethyl}-3-aza-bicyclo[3.1.0]hex-6-ylamine To a 100 mL round-bottomed flask equipped with condenser and N$_2$ inlet were added 160 mg (0.417 mmol) 3-{2-[4'-(6-amino-pyridin-2-yl)-biphenyl-4-yl]}-3-aza-bicyclo[3.1.0]hex-6-ylamine acetamide, 5 mL dry tetrahydrofuran, and 0.625 mL of a 2 M solution of borane methyl sulfide in tetrahydrofuran. The reaction was refluxed 12 hours, and additional 0.625 mL portion of borane methyl sulfide added along with a few mL tetrahydrofuran, and refluxing continued 12 hours (due to the limited solubility of the starting material in tetrahydrofuran). The reaction was cooled and evaporated, and 20 mL ethanol, 1 g. sodium carbonate, and 1 g cesium fluoride added, and the mixture refluxed 14 hours. The reaction was cooled and evaporated, taken up in water and ethyl acetate/methanol, and the organic layer separated, dried over sodium sulfate, and evaporated. The resulting solid, 80 mg (52%) was taken up in methylene chloride/methanol/ether and precipitated with 1 N HCl in ether, then evaporated. The residue was triturated with tetrahydrofuran to afford 48 mg (24%) of a white solid, mp 205° C. (dec. above this point).

$^1$H-NMR ($\delta$, CDCl$_3$): 1.33 (bs, 2H), 1.63 (bs, 1H), 2.60 (m, 2H), 2.71 (m, 2H), 3.05 (m, 2H), 3.59 (m, 2H), 4.56 (bs, 2H), 6.42 ($\delta$, J=8, 1H), 7.08 ($\delta$, J=7.5, 1H), 7.22 (m, 2H), 7.47–7.5 (m, 3H), 7.61 (m, 2H), 7.95 (m, 2H).

$^{13}$C-NMR ($\delta$, CDCl$_3$): 20.9, 32.2, 34.8, 55.0, 57.6, 107.4, 110.9, 126.9, 127.0, 128.9, 129.0, 136.3, 138.3, 138.5, 139.4, 141.0, 155.6, 158.5.

MS (%): 371 (100, parent+1).

Anal. Calc'd for C$_{24}$H$_{26}$N$_4$.3HCl.3H$_2$O: C, 53.99; H, 6.61; N, 10.49. Found: C, 53.79; H, 6.46; N, 8.70.

EXAMPLE 2

6-[4'-(4-Phenethyl-piperazin-1-ylmethyl)-biphenyl-4-yl]-pyridin-2-ylamine

A. 2-(2,5-Dimethylpyrrolyl)-6-[4'-(4-phenethyl-piperazin-1-ylmethyl)-biphenyl-4-yl]-pyridine To a 100 mL round-bottomed flask equipped with N$_2$ inlet were added 176 mg (0.50 mmol) 2-(2,5-dimethylpyrrolyl)-6-(4-(4'-formylbiphenyl-4-yl))-pyridine (Example 1B), 105 mg (0.55 mmol) 2-phenylethylpiperazine, 7 mL methanol, 30 uL (0.50 mmol) acetic acid, and 38 mg (0.60 mmol) sodium cyanoborohydride. The reaction was stirred at room temperature for 12 hours poured into aqueous sodium bicarbonate solution and extracted into ethyl acetate. The organic layer was washed with water and brine, dried over sodium sulfate, and evaporated. The residue was chromatographed on silica gel using methanol/methylene chloride as eluant to afford 190 mg (72%) of an oil.

$^1$H-NMR ($\delta$, CDCl$_3$): 2.26 (s, 6H), 2.5–2.7 (m, 8H), 2.83 (m, 2H), 3.60 (s, 2H) 5.97 (s, 2H), 7.15 ($\delta$, J=8, 1H), 7.2–7.3 (m, 5H), 7.44 (m, 2H), 7.62 (m, 2H), 7.72 (m, 2H), 7.79 ($\delta$, J=8, 1H), 7.87 (t, J=8, 1H), 8.16 (m, 2H).

$^{13}$C-NMR ($\delta$, CDCl$_3$): 13.6, 33.7, 53.1, 53.2, 60.6, 62.8, 107.0, 118.2, 119.8, 126.1, 126.9, 127.4, 128.4, 128.7, 128.8, 129.8, 137.2, 137.7, 138.6, 139.3, 140.3, 141.9, 151.7, 156.5.

MS (%): 527 (parent+1, 100).

B. 6-[4'-(4-Phenethyl-piperazin-1-ylmethyl)-biphenyl-4-yl]-pyridin-2-ylamine

To a 100 mL round-bottomed flask equipped with N$_2$ inlet were added 190 mg (0.361 mmol) 2-(2,5-dimethylpyrrolyl)-6-[4'-(4-phenethyl-piperazin-1-ylmethyl)-biphenyl-4-yl]-pyridine, 126 mg (1.81 mmol) hydroxylamine hydrochloride, 1 mL water, and 5 mL ethanol. The reaction was heated at reflux for 36 hours followed by treatment with an additional 50 mg hydroxylamine hydrochloride and refluxing for 24 hours. The reaction was cooled, poured into dilute aqueous hydrochloric acid, and washed with ethyl acetate. The aqueous layer was adjusted to pH 10 with 1 N sodium hydroxide solution and extracted with ethyl acetate. The organic layer was washed with brine, dried over sodium sulfate, and evaporated. The residue was converted to the hydrochloride salt using 1 N HCl in ether to afford 110 mg (55%) of a solid, mp 267–269° C.

$^1$H-NMR ($\delta$, CDCl$_3$): 2.5–2.7 (m, 8H), 2.81 (m, 2H), 3.57 (s, 2H), 4.66 (bs, 2H), 6.42 ($\delta$, J=8, 1H), 7.10 ($\delta$, J=7.5, 1H), 7.21 (m, 3H), 7.26 (m, 2H), 7.41 (m, 2H), 7.47 (t, J=8, 1H), 7.59 (m, 2H), 7.66 (m, 2H), 8.00 (m, 2H).

$^{13}$C-NMR ($\delta$, CDCl$_3$): 33.7, 53.1, 53.2, 60.6, 62.8, 107.2, 110.8, 126.1, 126.9, 127.2, 127.3, 128.4, 128.7, 129.7, 137.4, 138.4, 139.5, 140.4, 141.0, 155.7, 158.4.

MS (%): 449 (parent+1, 100).

Anal. Calc'd for C$_{30}$H$_{32}$N$_4$.3HCl.3/2H$_2$O: C, 61.59; H, 6.55; N, 9.58. Found: C, 61.64; H, 6.31; N, 9.51.

EXAMPLE 3

3-[4'-(6-Amino-pyridin-2-yl)-biphenyl-4-ylmethyl]-3-aza-bicyclo[3.1.0]hex-6-ylamine Prepared as in Example 2, using 3-aza-bicyclo[3.1.0]hex-6-ylamine t-butyl carbamate for the reductive amination step (2A) in 67% yield as an oil:

$^1$H-NMR ($\delta$, CDCl$_3$): 1.46 (s, 9H), 1.52 (bs, 2H), 2.26 (s, 6H), 2.43 and 3.11 (multiplets, 4H), 2.94 (m, 1H), 3.61 (s, 2H), 5.97 (s, 2H), 7.14 (dd, J=1,8, 1H), 7.34 (m, 2H), 7.57 (m, 2H), 7.70 (m, 2H), 7.78 ($\delta$, J=7, 1H), 7.87 (t, J=8, 1H), 8.16 (m, 2H).

$^{13}$C-NMR ($\delta$, CDCl$_3$): 13.6, 24.6, 28.4, 30.6, 54.2, 58.6, 107.0, 118.2, 119.8, 126.8, 127.1, 127.3, 127.5, 128.7, 128.9, 132.1, 137.1, 138.6, 138.9, 142.0, 151.7, 156.5.

MS (%): 535 (parent+1, 100).

Followed by removal of the protecting groups with hydroxylamine hydrochloride in aqueous ethanol (as in Example 2B) and treatment with trifluoroacetic acid in methylene chloride at room temperature for 3 hours to give overall 65% yield of the trifluoroacetate salt, triturated with tetrahydrofuran, mp 112–119° C.:

$^1$H-NMR (δ, TFA salt in CDCl$_3$): 2.33 (bs, 2H), 2.99 (bs, 1H), 3.29 (m, 2H), 3.70 (m, 2H), 4.41 (s, 2H), 6.98 (δ, J=8, 1H), 7.20 (δ, J=7.5, 1H), 7.60 (m, 2H), 7.78 (m, 2H), 7.88 (m, 2H), 7.98 (t, J=8, 1H).

$^{13}$C-NMR (δ, TFA salt in CDCl$_3$): 23.7, 27.5, 57.1, 60.1, 6.9., 113.1, 113.9, 129.9, 130.0, 130.1, 132.7, 133.4, 133.6, 143.5, 145.1, 146.7, 149.1, 157.9.

MS (%): 357 (parent+1, 100).

Anal. Calc'd for C$_{23}$H$_{24}$N$_4$.3(C$_2$F$_3$O$_2$H).1/2H$_2$O: C, 49.23; H, 3.99; N, 7.92. Found: C, 49.14; H, 3.90; N, 7.80.

EXAMPLE 4

3-[4'-(6-Amino-pyridin-2-yl)-biphenyl-3-ylmethyl]-3-aza-bicyclo[3.1.0]hex-6-ylamine A. 2-(2,5-Dimethylpyrrolyl)-6-(4-(3-tolyl)phenyl))-pyridine Prepared as in Example 1 B using 3-tolyl boronic acid as an oil in 39% yield.

$^1$H-NMR (δ, CDCl$_3$) 2.32 (s, 6H), 2.49 (s, 3H), 6.03 (s, 2H), 7.19 (dd, J=1,8, 1H), 7.25 (m, 1H), 7.41 (t, J=7.5, 1H), 7.53 (m, 2H), 7.77 (m, 2H), 7.81 (dd, J=1,8, 1H), 7.90 (t, J=8, 1H), 8.21 (m, 2H).

$^{13}$C-NMR (δ, CDCl$_3$) 13.6, 21.7, 107.1, 118.3, 119.9, 124.3, 127.0, 127.4, 127.5, 127.9, 128.5, 128.7, 128.8, 137.2, 138.5, 138.7, 140.5, 142.3, 151.8, 156.5.

MS (%): 339 (parent+1, 100).

B. 2-Phthamimido-6-(4-(3-tolyl)phenyl))-pyridine

To a 100 mL round-bottomed flask equipped with condenser and N$_2$ inlet were added 200 mg (0.592 mmol) 2-(2,5-dimethylpyrrolyl)-6-(4-(3-tolyl)phenyl))-pyridine, 206 mg (2.96 mmol) hydroxylamine hydrochloride, 4 mL ethanol and 1 mL water. The reaction was refluxed 36 hours cooled, and poured into dilute aqueous sodium bicarbonate solution and extracted into ethyl acetate. The organic layer was separated, washed with brine, and dried. The residue, as a brown oil, 138 mg (90%), was taken up in 10 mL dry toluene and treated with 116 mg (0.531 mmol) N-carbethoxyphthalimide. The resulting solution was refluxed 20 hours cooled and evaporated. The residue was chromatographed on silica gel using hexane/ethyl acetate as eluant to give 130 mg (56% overall) of an oil.

$^1$H-NMR (δ, CDCl$_3$): 2.40 (s, 3H), 7.15 (m, IH), 7.34 (m, 2H), 7.42 (m, 2H), 7.65 (m, 2H), 7.79 (m, 3H), 7.92 (m, 3H), 8.07 (m, 2H).

$^{13}$C-NMR (δ, CDCl$_3$): 21.6, 119.9, 120.1, 123.5, 123.9, 124.2, 122.2, 122.4, 127.5, 127.9, 128.3, 128.7, 131.9, 133.7, 134.2, 134.5, 135.3, 138.4, 139.0, 157.3, 166.8.

MS (%): 391 (parent+1, 100).

C. 3-[4'-(6-Phthalimido-pyridin-2-yl)-biphenyl-3-ylmethyl]-3-aza-bicyclo[3.1.0]hex-6-ylamine t-butyl carbamate To a 100 mL round-bottomed flask equipped with condenser and N2 inlet were added 130 mg (0.333 mmol) 2-phthamimido-6-(4-(3-tolyl)phenyl))-pyridine, 59 mg (0.333 mmol) N-bromosuccinimide, 10 mg diazo-bis(1-cyanocyclohexane), and 10 mL carbon tetrachloride. The reaction was refluxed 1 hour an additional 10 mg of diazo-bis(1-cyanocyclohexane) added, and refluxing continued 1 hour. The reaction was then cooled, filtered and evaporated. The residue was taken up in 10 mL dry acetonitrile and treated with 66 mg (0.333 mmol) 3-aza-bicyclo[3.1.0]hex-6-ylamine and 28 mg (0.333 mmol) sodium bicarbonate. The reaction was refluxed 12 hours cooled, and evaporated. The residue was taken up in ethyl acetate and water, and the organic layer separated, washed with brine, dried over sodium sulfate and evaporated. The residue was chromatographed on silica gel using methanol/methylene chloride as eluant to afford 130 mg (67%) of an oil.

$^1$H-NMR (δ, CDCl$_3$): 1.38 (s, 9H), 1.6–1.8 (m, 2H), 3.2–3.5 (m, 5H), 3.57 (m, 2H), 7.15 (dd, J=1,8, 1H), 7.2–7.5 (m, 4H), 7.65 (m, 3H), 7.78 (m, 3H), 7.92 (m, 2H), 8.05 (m, 2H).

$^{13}$C-NMR (δ, CDCl$_3$): 28.3, 47.6, 50.5, 54.1, 62.1, 116.5, 118.8, 119.9, 120.1, 123.9, 126.5, 127.3, 127.4, 127.5, 128.8, 129.2, 131.8, 134.5, 136.4, 136.8, 138.9, 155.1, 157.2, 165.6, 166.7, 169.6, 169.8.

MS (%): 587 (parent+1, 100).

D. 3-[4'-(6-Amino-pyridin-2-yl)-biphenyl-3-ylmethyl]-3-aza-bicyclo[3.1.0]hex-6-ylamine To a 100 mL round-bottomed flask equipped with condenser and N$_2$ inlet were added 130 mg (0.222 mmol) 3-[4'-(6-phthalimido-pyridin-2-yl)-biphenyl-3-ylmethyl]-3-aza-bicyclo[3.1.0]hex-6-ylamine t-butyl carbamate, 20 mL methanol and 0.3 mL hydrazine. The reaction was heated at 50° C. for 2.5 hours cooled, and evaporated. The residue was taken up in ethyl acetate and washed with 0.2 N sodium hydroxide solution, water and brine, dried over sodium sulfate, and evaporated.

The residue, 110 mg, was taken up in 6 mL dry methylene chloride and treated with 1.5 mL trifluoroacetic acid at room temperature for 2 hours. The reaction was evaporated and taken up in ethyl acetate/0.3 N hydrochloric acid. The aqueous layer was separated, the pH adjusted to 10 with 6 N sodium hydroxide solution, and extracted into ethyl acetate. The organic layer was washed with brine, dried over sodium sulfate, and evaporated. The resulting oil was converted to the hydrochloride using 1 N HCl in ether and triturated with tetrahydrofuran to afford 21 mg (20%) of a solid, mp 184–196° C.

$^1$H-NMR (δ, CDCl$_3$): 1.37 (bs, 2H), 1.51 (bs, 1 H), 2.46 and 3.02 (multiplets, 4H), 3.64 (s, 2H), 4.60 (bs, 2H), 6.46 (δ, J=8, 1H), 7.13 (δ, J=7.5, 1H), 7.2–7.6 (m, 5H), 8.00 (m, 2H).

$^{13}$C-NMR (δ, CDCl$_3$): 14.0, 38.7, 54.5, 59.2, 107.1, 110.8, 115.1, 125.7, 126.8, 127.1, 127.3, 127.7, 128.6, 138.3, 138.5, 139.0, 140.6, 141.3, 155.7, 158.3.

MS (%): 357 (parent+1, 100).

EXAMPLE 5

2-Amino-N-[4'-(6-amino-pyridin-2-yl)-biphenyl-3-yl]-propionamide

A. 2-(2,5-Dimethylpyrrolyl)-6-(4-(3-nitrophenyl)phenyl))-pyridine

Prepared as in Example 1B, using 3-nitrophenyl boronic acid as an oil in 66% yield.

$^1$H-NMR (δ, CDCl$_3$): 2.24 (s, 6H), 5.96 (s, 2H), 7.15 (δ, J=8, 1H), 7.54 (t, J=8, 1H), 7.67 (m, 2H), 7.76 (m, 1H), 7.88 (m, 2H), 8.15 (m, 3H), 8.42 (bs, 1H).

$^{13}$C-NMR (δ, CDCl$_3$): 13.6, 107.3, 118.4, 120.2, 121.9, 123.2, 123.4, 127.6, 128.6, 129.9, 132.9, 138.5, 138.9, 139.2, 141.9, 148.7, 151.8, 155.8.

MS (%): 370 (parent+1, 100).

B. 2-(2,5-Dimethylpyrrolyl)-6-(4-(3-aminophenyl)phenyl))-pyridine

To a 100 mL round-bottomed flask equipped with condenser and $N_2$ inlet were added 520 mg (1.41 mmol) 2-(2,5-dimethylpyrrolyl)-6-(4-(3-nitrophenyl)phenyl))-pyridine, 445 mg (7.05 mmol) ammonium formate, 10 mL ethanol, and 80 mg 10% palladium on carbon (a few mL 1,2-dichloroethane added to dissolve the nitro compound). The reaction was refluxed 40 min, cooled, and filtered with ethanol through Celite. The filtrate was evaporated, taken up in ethyl acetate/dilute aqueous sodium hydroxide solution, and the organic layer separated and washed with brine, dried over sodium sulfate, and evaporated to an oil, 400 mg (84%).

$^1$H-NMR (δ, CDCl$_3$): 2.26 (s, 6H), 3.77 (bs, 2H), 5.99 (s, 2H), 6.67 (m, 1H), 6.92 (bs, 1H), 7.04 (m, 1H), 7.14 (m, 1H), 7.23 (t, J=8, 1H), 7.67 (m, 2H), 7.75 (δ, J=8, 1H), 8.14 (m, 2H).

$^{13}$C-NMR (δ, CDCl$_3$): 13.5, 107.0, 113.6, 114.4, 117.3, 118.2, 119.8, 127.1, 127.3, 128.6, 129.7, 137.1, 138.6, 141.4, 142.3, 147.0, 151.6, 156.4.

MS (%): 340 (parent+1, 100).

C. 2-(t-Butylcarbamoylamino)-N-[4'-(6-(2,5-dimethylpyrrolyl)-pyridin-2-yl)-biphenyl-3-yl]-propionamide To a 100 mL round-bottomed flask equipped with $N_2$ inlet were added 200 mg (0.590 mmol) 2-(2,5-dimethylpyrrolyl)-6-(4-(3-aminophenyl)phenyl))-pyridine, 117 mg (0.590 mmol) N-t-butoxycarbonylalanine, 113 mg (0.590 mmol) EDAC, 159 mg (1.30 mmol) 4-dimethylaminopyridine, and 10 mL dry acetonitrile. The reaction was stirred at room temperature for 12 hours evaporated, and the residue chromatographed on silica gel using methanol/methylene chloride as eluant to afford 230 mg (76%) of an oil.

$^1$H-NMR (δ, CDCl$_3$): 1.46 (s, 9H), 1.48 (δ, J=7, 3H), 2.24 (s, 6H), 4.55 (m, 1H), 5.62 (m, 1H), 5.96 (s, 2H), 7.11 (δ, J=8, 1H), 7.23 (m, 2H), 7.47 (m, 1H), 7.57 (m, 2H), 7.69 (m, 1H), 7.81 (m, 2H), 8.05 (m, 2H).

$^{13}$C-NMR (δ, CDCl$_3$): 13.5, 18.0, 28.3, 50.9, 80.4, 106.9, 118.2, 118.9, 119.7, 122.6, 127.1, 127.3, 128.6, 129.2, 137.2, 138.5, 138.6, 140.9, 141.4, 151.6, 156.3, 171.8.

MS (%): 511 (parent+1, 100).

D. 2-Amino-N-[4'-(6-amino-pyridin-2-yl)-biphenyl-3-yl]-propionamide

To a 100 mL round-bottomed flask equipped with N2 inlet were added 230 mg (0.451 mmol) 2-(t-butylcarbamoylamino)-N-[4'-(6-(2,5-dimethylpyrrolyl)-pyridin-2-yl)-biphenyl-3-yl]-propionamide and 25 mL ethyl acetate. The solution was cooled to 0° C. and saturated with HCl, then stirred at 0° C. for 30 minutes and 1 hour at room temperature. The resulting precipitate was collected and dissolved in 20 mL methanol, treated with 1 mL water and 157 mg (2.255 mmol) hydroxylamine hydrochloride, and refluxed 2 days. The reaction was cooled, evaporated, and taken up in ethyl acetate/dilute hydrochloric acid. The aqueous layer was separated, the pH adjusted to 10 with 6 N sodium hydroxide solution, and extracted with ethyl acetate. The organic layer was washed with brine, dried over sodium sulfate, and evaporated. The oil was taken up in methylene chloride, treated with decolorizing carbon, filtered through Celite, and evaporated. The resulting oil (90 mg) was converted to the hydrochloride salt using 1 N HCl in ether to afford a solid, 73 mg (40%), mp >215° C. (dec.).

$^1$H-NMR (δ, CDCl$_3$): 1.39 (δ, J=7, 3H), 3.57 (q, J=7, 1H), 4.66 (bs, 2H), 6.40 (δ, J=8, 1H), 7.05 (δ, J=7.5, 1H), 7.34 (m, 2H), 7.43 (t, J=8, 1H), 7.62 (m, 4H), 7.93 (m, 2H), 9.57 (bs, 1H).

$^{13}$C-NMR (δ, CDCl$_3$): 21.5, 51.1, 107.2, 110.7, 117.9, 118.3, 122.6, 127.1, 127.2, 129.3, 138.3, 138.6, 140.6, 141.3, 155.4, 158.3, 173.9.

MS (%): 333 (parent+1, 100).

IR (KBr, cm.$^{-1}$): 1657 (C=O).

EXAMPLE 6

2-Amino-N-[4'-(6-amino-pyridin-2-yl)-biphenyl-3-yl]-3-phenyl-propionamide

Prepared as in Example 5, using t-butoxycarbonylphenylalanine, with the coupling step proceeding in 58% yield, and the deblocking in 57% yield to afford the product as the hydrochloride salt, mp 180–200° C. (dec.)

$^1$H-NMR (δ, CDCl$_3$): 2.81 and 3.37 (multiplets, 2H), 3.74 (dd, J=4,9, 1H), 4.62 (bs, 2H), 6.43 (δ, J=8, 1H), 7.10 (δ, J=7.5, 1H), 7.2–7.4 (m, 8H), 7.47 (t, J=8, 1H), 7.65 (m, 3H), 7.97 (m, 2H), 9.53 (bs, 1H).

$^{13}$C-NMR (δ, CDCl$_3$): 40.6, 56.8, 107.2, 110.8, 118.0, 118.5, 122.8, 126.9, 127.0, 127.1, 127.2, 128.8, 129.2, 129.4, 1137.6, 138.1, 138.4, 138.6, 140.7, 141.4, 155.4, 158.2, 172.4.

MS (%): 409 (parent+1, 100).

EXAMPLE 7

6-[4-(1-Benzyl-1,2,5,6-tetrahydro-pyridin-3-yl)-phenyl]-pyridin-2-ylamine

A. 2-(2,5-Dimethylpyrrolyl)-6-[4-(pyrid-3-yl)-phenyl]-pyridine

To a 100 mL round-bottomed flask equipped with condenser and $N_2$ inlet were added 271 mg (2.20 mmol) 3-pyridylboronic acid (*Rec. Trav. Chim.*, 93, 21 (1974)), 720 mg (2.20 mmol) 2-(2,5-dimethylpyrrolyl)-6-(4-bromophenyl)-pyridine, 933 mg (8.81 mmol) sodium carbonate, 128 mg (0.110 mmol) tetrakistriphenylphosphine palladium, 9 mL ethanol, and 1 mL water. The mixture was refluxed 20 hours 100 mg 3-pyridiylboronic acid added, and refluxing continued for 2 hours. The reaction was then cooled, poured into water and extracted into ethyl acetate. The organic layer was washed with brine, dried over sodium sulfate, and evaporated. The residue was chromatographed on silica gel using methanol/methylene chloride as eluant to afford the product as an oil, 350 mg (49%).

$^1$H-NMR (δ, CDCl$_3$): 2.25 (s, 6H), 5.97 (s, 2H), 7.12 (δ, J=8, 1H), 7.31 (dd, J=5,8, 1H), 7.64 (m, 2H), 7.74 (δ, J=8, 1H), 7.83 (m, 2H), 8.16 (m, 2H), 8.59 (m, 1H), 8.90 (m, 1H).

$^{13}$C-NMR (δ, CDCl$_3$): 13.6, 107.2, 118.3, 120.1, 123.7, 127.4, 127.6, 128.1, 128.6, 129.1, 134.2, 135.9, 138.6, 138.8, 148.2, 148.5, 128.8, 151.8, 156.0.

MS (%): 326 (parent+1, 100).

B. 2-(2,5-Dimethylpyrrolyl)-6-[4-(1-benzyl-1,2,5,6-tetrahydro-pyridin-3-yl)-phenyl]-pyridine To a 100 mL round-bottomed flask equipped with condenser and $N_2$ inlet were added 350 mg (1.077 mmol) 2-(2,5-dimethylpyrrolyl)-6-[4-(pyrid-3-yl)-phenyl]-pyridine, 10 mL dry acetonitrile, and 128 uL (1.077 mmol) benzyl bromide. The reaction was heated at 70° C. for 14 hours cooled, evaporated, and the residue taken up in 5 mL ethanol and 4 mL water, and treated with 149 mg (2.37 mmol) sodium cyanoborohydride (a few mL dichloromethane was added to improve solubility). The reaction was stirred at room temperature for 20 hours poured into dilute aqueous sodium bicarbonate solution, and extracted with ethyl acetate. The organic layer was washed with brine, dried over sodium sulfate, and evaporated. The residue was chromatographed on silica gel using methanol/methylene chloride as eluant to afford two product fractions:

2-(2,5-dimethylpyrrolyl)-6-[4-(1-benzyl-1,2,5,6-tetrahydro-pyridin-3-yl)-phenyl]-pyridine as an oil, 135 mg (30%):

$^1$H-NMR (δ, CDCl$_3$): 2.26 (s, 6H), 2.41 (m, 2H), 2.67 (m, 2H), 3.45 (m, 2H), 3.76 (s, 2H), 5.98 (s, 2H), 6.28 (bs, 1H), 7.13 (δ, J=8, 1H), 7.3–7.5 (m, 7H), 7.73 (δ, J=8, 1H), 7.85 (t, J=8, 1H), 8.05 (m, 2H).

$^{13}$C-NMR (δ, CDCl$_3$): 13.6, 26.6, 49.2, 54.6, 62.9, 107.0, 118.1, 119.7, 123.5, 125.2, 126.9, 127.2, 128.4, 128.7, 129.3, 134.8, 136.9, 138.2, 138.6, 141.1, 151.7, 156.5.

MS (%): 420 (parent+1, 100), and 2-(2,5-dimethylpyrrolyl)-6-[4-(1-benzyl-piperidin-3-yl)-phenyl]-pyridine, 170 mg (37.5%):

$^1$H-NMR (δ, CDCl$_3$): 1.82 (m, 4H), 2.23 (s, 6H), 2.67 (m, 1H), 2.9–3.1 (m, 4H), 3.66 (s, 2H), 5.95 (s, 2H), 7.12 (δ, J=8, 1H), 7.2–7.5 (m, 7H), 7.73 (δ, J=8, 1H), 7.86 (t, J=8, 1H), 8.01 (m, 2H).

$^{13}$C-NMR (δ, CDCl$_3$): 13.6, 25.2, 31.3, 42.3, 53.5, 60.3, 63.2, 107.0, 118.2, 119.7, 127.1, 127.6, 127.7, 128.4, 128.5, 128.7, 129.5, 129.9, 133.3, 136.7, 138.7, 151.6, 156.7.

MS (%): 420 (parent+1, 100).

C. 6-[4-(1-Benzyl-1,2,5,6-tetrahydro-pyridin-3-yl)-phenyl]-pyridin-2-ylamine

To a 100 mL round-bottomed flask equipped with condenser and N$_2$ inlet were added 135 mg (0.322 mmol) 2-(2,5-dimethylpyrrolyl)-6-[4-(1-benzyl-1,2,5,6-tetrahydro-pyridin-3-yl)-phenyl]-pyridine, 112 mg (1.61 mmol) hydroxylamine hydrochloride, 5 mL ethanol, and 1 mL water. The reaction was refluxed 40 hours cooled, and the resulting precipitate, 6-[4-(1-benzyl-1,2,5,6-tetrahydro-pyridin-3-yl)-phenyl]-pyridin-2-ylamine dihydrochloride, filtered and dried, 22 mg (16.5%), mp 270–272° C. Additional material was recovered from the filtrate, 60 mg (55%) of the free base as an oil.

$^1$H-NMR (δ, CDCl$_3$): 2.35 (m, 2H), 2.64 (m, 2H), 3.40 (m, 2H), 3.71 (s, 2H), 4.58 (bs, 2H), 6.21 (bs, 1H), 6.40 (δ, J=8, 1H), 7.04 (δ, J=7.5, 1H), 7.2–7.4 (m, 7H), 7.45 (t, J=8, 1H), 7.84 (m, 2H).

$^{13}$C-NMR (δ, CDCl$_3$): 26.5, 49.1, 54.6, .62.8, 107.1, 110.7, 122.9, 125.0, 126.7, 126.8, 127.1, 128.3, 129.3, 134.9, 138.1, 138.2, 138.3, 138.4, 155.8.

MS (%): 342 (parent+1, 100).

Anal. Calc'd for C$_{23}$H$_{23}$N$_3$.2HCl.1/2H$_2$O: C, 65.25; H, 6.19; N, 9.92. Found: C, 65.62; H, 6.42; N, 9.93.

EXAMPLE 8

6-[4-(1-Benzyl-piperidin-3-yl)-phenyl]-pyridin-2-ylamine

Prepared as in Example 7C using the intermediate from Example 7B, to afford 50 mg (30%) of a solid, mp 55–70° C.

$^1$H-NMR (δ, CDCl$_3$): 1.75 (m, 2H), 2.0 (m, 2H), 2.62 (m, 1H), 2.8–3.0 (m, 4H), 3.55 (s, 2H), 4.58 (bs, 2H), 6.40 (δ, J=8, 1H), 7.05 (δ, J=8, 1H), 7.2–7.4 (m, 7H), 7.44 (t, J=8, 1H), 7.82 (m, 2H).

$^{13}$C-NMR (δ, CDCl$_3$): 25.7, 31.7, 42.7, 53.7, 61.0, 63.6, 106.9, 110.7, 126.8, 127.0, 127.5, 128.2, 128.3, 129.2, 129.3, 133.8, 137.8, 138.3, 145.7, 156.1, 158.3.

MS (%): 344 (parent+1, 100).

EXAMPLE 9

6-[4-(1-Benzyl-piperidin-2-ylmethyl)-phenyl]-pyridin-2-ylamine

A. N-Benzyl-2-(4-bromobenzyl)-piperidine

To a 100 mL round-bottomed flask equipped with N$_2$ inlet were added 250 mg (0.984 mmol) 2-(4-bromobenzyl)-piperidine (prepared as described in *Tetrahedron Letters*, 7, 631 (1977)), 110 uL (1.08 mmol) benzaldehyde, 7 mL methanol, 74 mg (1.18 mmol) sodium cyanoborohydride, and a few drops of acetic acid. The reaction was stirred at room temperature, followed by additional benzaldehyde, sodium cyanoborohydride, and acetic acid, for a total of 16 hours then poured into dilute aqueous sodium bicarbonate solution, and extracted into ethyl acetate. The organic layer was washed with brine, dried over sodium sulfate, and evaporated. The residue was chromatographed on silica gel using methanol/methylene chloride as eluant, and the product further purified by conversion to the hydrochloride salt in ether followed by basification using aqueous sodium hydroxide solution to afford 175 mg (52%) of an oil.

$^1$H-NMR (δ, CDCl$_3$): 1.29 (m, 2H), 1.53 (m, 3H), 1.6 (m, 1H), 2.26 and 2.79 (multiplets, 2H), 2.60 (m, 2H), 3.15 (dd, J=3,12, 1H), 3.77 (Ab$_q$, J=13.5, Dn=41, 2H), 7.00 (m, 1H), 7.2–7.4 (m, 8H).

$^{13}$C-NMR (δ, CDCl$_3$): 22.4, 24.9, 28.9, 36.0, 51.0, 58.2, 61.5, 127.0, 127.2, 127.6, 128.3, 128.5, 129.2, 131.1, 131.4, 139.0, 140.9.

MS (%): 344/346 (parent+1, Br$^{79}$/Br$^{81}$, 100).

B. 2-(2,5-Dimethylpyrrolyl)-6-[4-(1-benzyl-piperidin-2-ylmethyl)-phenyl]-pyridine To a 100 mL 3N round-bottomed flask equipped with septum and N$_2$ inlet were added 175 mg (0.509 mmol) N-benzyl-2-(4-bromobenzyl)-piperidine and 7 mL dry ether. The solution was cooled to −70° C., and 0.38 mL (0.610 mmol) of a 1.6 M solution of butyl lithium in hexane added dropwise over 1 minutes. The reaction was stirred at −70° C. for 5 min, then warmed to room temperature over 20 minutes. To the stirring reaction was then added a solution of 105 mg (0.610 mmol) 2-(2,5-dimethylpyrrolyl)-pyridine in 5 mL dry ether, and the reaction, turning dark orange, was stirred at room temperature for 4 hours then quenched with aqueous ammonium chloride solution. After extraction into ethyl acetate, the organic layer was washed with brine, dried over sodium sulfate for 16 hours to effect air-oxidation to the pyridine, and evaporated. The residue was chromatographed on silica gel using methanol/methylene chloride as eluant to afford 36 mg (16%) of an oil.

$^1$H-NMR (δ, CDCl$_3$): 1.30 (m, 2H), 1.55 (m, 3H), 1.64 (m, 1H), 2.22 (s, 6H), 2.6–2.9 (m, 4H), 3.11 and 3.25 (multiplets, 1H), 3.54 and 4.07 (multiplets, 2H), 5.93 (s, 2H), 7.01 (δ, J=8, 1H), 7.2–7.4 (m, 7H), 7.72 (δ, J=8, 1H), 7.85 (t, J=8, 1H), 7.98 (m, 2H).

$^{13}$C-NMR (δ, CDCl$_3$): 13.5, 22.3, 25.0, 29.0, 50.8, 58.2, 61.5, 65.2, 106.9, 118.1, 119.6, 126.9, 127.0, 127.6, 128.3, 128.5, 128.7, 129.0, 129.1, 129.8, 131.1, 131.3, 138.5, 141.5, 155.5, 157.0.

MS (%): 436 (parent+1, 100).

C. 6-[4-(1-Benzyl-piperidin-2-ylmethyl)-phenyl]-pyridin-2-ylamine

To a 100 mL round-bottomed flask equipped with condenser and N$_2$ inlet were added 36 mg (0.0827 mmol) 2-(2,5-dimethylpyrrolyl)-6-[4-(1-benzyl-piperidin-2- ylmethyl)-phenyl]-pyridine, 29 mg (0.414 mmol) hydroxylamine hydrochloride, 4 mL ethanol and 1 mL water. The reaction was refluxed 84 h (additional hydroxylamine hydrochloride was used to complete the reaction), cooled, poured into dilute hydrochloric acid, and washed with ethyl acetate. The aqueous layer was adjusted to pH 10 with 6 N sodium hydroxide solution and extracted with ethyl acetate. The organic layer was washed with brine, dried over sodium sulfate, and evaporated. The resulting oil was converted to the hydrochloride salt using 1 N HCl in ether to afford a solid, 17 mg (48%), mp 70–85° C.

hu 1H-NMR ($\delta$, CDCl$_3$): 1.32 (m, 2H), 1.52 (m, 3H), 1.63 (m, 1H), 2.6–2.8 (m, 2H), 3.21 (m, 1H), 3.53 (m, 2H), 4.08 (m, 2H), 4.50 (bs, 2H), 6.42 ($\delta$, J=8, 1H), 7.05 ($\delta$, J=7.5, 1H), 7.2–7.4 (m, 7H), 7.47 (t, J=8, 1H), 7.81 (m, 2H).

$^{13}$C-NMR ($\delta$, CDCl$_3$): 22.4, 23.8, 25.3, 36.2, 38.7, 50.9, 61.8, 106.8, 110.8, 126.7, 126.8, 128.2, 128.8, 128.9, 129.0, 129.6, 131.1, 131.3, 138.3, 141.0, 156.2, 158.6.

MS (%): 358 (parent+1, 100).

Anal. Calc'd for $C_{24}H_{27}N_3 \cdot 2HCl \cdot 3H_2O$: C, 59.50; H, 7.28; N, 8.67. Found: C, 59.54; H, 6.98; N, 7.32.

EXAMPLE 10

6-{4-[1-(2,2-Diphenyl-ethyl)-piperidin-2-ylmethyl]-phenyl}-pyridin-2-ylamine

Prepared as in Example 9, using diphenylacetaldehyde in the step analogous to 9A, 59% yield, followed by a 33% yield in the organolithium addition, and a 31% yield in the deblocking to afford the product as the dihydrochloride salt, mp 168–180° C.

$^1$H-NMR ($\delta$, CDCl$_3$): 1.4–1.7 (m, 6H), 2.4–3.4 (series of multiplets, 8H), 4.49 (bs, 2H), 6.43 ($\delta$, J=8, 1H), 7.04 ($\delta$, J=7.5, 1H), 7.11 (m, 2H), 7.2–7.4 (m, 10H), 7.47 (t, J=8, 1H), 7.79 (m, 2H).

$^{13}$C-NMR ($\delta$, CDCl$_3$): 23.0, 23.8, 29.7, 38.7, 49.5, 50.5, 59.6, 61.6, 106.8, 110.8, 126.2, 126.7, 128.3, 129.5, 130.9, 138.4, 141.9, 144.0, 156.0, 158.2.

MS (%): 448 (parent+1, 100).

EXAMPLE 11

6-[3-(2-Dimethylamino-cyclopentylmethyl)-phenyl]-pyridin-2-ylamine

A. 2-(4-((2-(2,5-Dimethylpyrrolyl))-pyrid-6-yl)benzylidene)cyclopentanone

To a 100 mL round-bottomed flask equipped with Dean-Stark trap topped with a condenser and N$_2$ inlet were added 552 mg (2.0 mmol) 2-(2,5-dimethylpyrrolyl)-6-(4-formylphenyl)-pyridine, 20 mL benzene, 0.384 mL (2.4 mmol) 4-morpholino-1-cyclohexene, and 10 mg camphorsulfonic acid. The solution was refluxed with removal of water for 13 hours cooled, and 25 mL 3N hydrochloric acid added. The mixture was stirred at room temperature for 1 hour then diluted with ethyl acetate and water. The organic layer was separated, washed with aqueous sodium bicarbonate solution and brine, dried over sodium sulfate, and evaporated. The crude oil solidified on standing, 460 mg (~100%), and was used directly in the next step.

$^1$H-NMR ($\delta$, CDCl$_3$): 1.95 (m, 2H), 2.195 (s, 6H), 2.33 (t, J=8, 2H), 2.91 (m, 2H), 5.91 (s, 2H), 7.09 ($\delta$, J=8, 1H), 7.36 (bs, 1H), 7.55 (m, 2H), 7.71 ($\delta$, J=8, 1H), 8.07 (m, 2H).

$^{13}$C-NMR ($\delta$, CDCl$_3$): 13.5, 20.0, 29.3, 37.6, 107.1, 118.4, 120.1, 127.0, 128.2, 128.1, 130.8, 131.2, 136.4, 136.7, 138.8, 151.7, 155.6.

MS (%): 343 (parent+1, 100).

B. 2-(4-((2-(2,5-Dimethylpyrrolyl))-pyrid-6-yl)benzyl)cyclopentanone

To a 100 mL round-bottomed flask equipped with condenser and N$_2$ inlet were added the crude material from above (2 mmol) and 4 mL 1,2-dichloroethane. After dissolution, 25 mL ethanol was added, followed by 631 mg (10 mmol) ammonium formate and 100 mg 10% palladium-on-carbon. The mixture was refluxed 1 hours then treated with additional ammonium formate and palladium-on-carbon (Pd-C) and refluxed for 1 hour. The reaction was then cooled and filtered through Celite with ethanol and methylene chloride. The filtrate was evaporated, taken up in ethyl acetate and aqueous sodium bicarbonate solution, the organic layer separated, washed with brine, dried over sodium sulfate and evaporated. The residue was chromatographed on silica gel using ethyl acetate/hexane as eluant to afford 410 mg (60% overall) of a foam.

$^1$H-NMR ($\delta$, CDCl$_3$): 1.56 (m, 1H), 1.70 (m, 1H), 1.93 (m, 1H), 2.06 (m, 2H), 2.24 (s, 6H), 2.29 (m, 1H), 2.36 (m, 1H), 2.61 (m, 1H), 3.19 (dd, J=4,14, 1H), 5.95 (s, 2H), 7.10 ($\delta$, J=8, 1H), 7.27 (m, 2H), 7.71 ($\delta$, J=8, 1H), 7.83 (t, J=8, 1H), 8.01 (m, 2H).

$^{13}$C-NMR ($\delta$, CDCl$_3$): 13.5, 20.5 29.0, 35.3, 38.1, 50.8, 107.0, 118.1, 119.6, 126.9, 128.5, 129.3, 136.3, 138.7, 141.5, 151.6, 156.6.

IR (neat, cm.$^{-1}$): 1735 (C=O).

MS (%): 345 (parent+1, 100).

C. 2-(2,5-Dimethylpyrrolyl)-6-[3-(2-dimethylamino-cyclopentylmethyl)-phenyl]-pyridine To a 100 mL round-bottomed flask equipped with condenser and N$_2$ inlet were added 205 mg (0.596 mmol) 2-(4-((2-(2,5-dimethylpyrrolyl))-pyrid-6-yl)benzyl)cyclopentanone, 10 mL methanol, 486 mg (5.96 mmol) dimethylamine hydrochloride, 45 mg (0.715 mmol) sodium cyanoborohydride, and 41 uL (0.715 mmol) acetic acid. The reaction was heated at 50° C. for 40 hours, cooled, and poured into aqueous sodium bicarbonate solution. The mixture was extracted with ethyl acetate, and the organic layer washed with brine, dried over sodium sulfate, and evaporated. The residue was chromatographed on silica gel using methanol/methylene chloride (with a small amount of triethylamine) as eluant to afford both diastereomers as an oil.

Less polar diastereomer, 140 mg (63%):

$^1$H-NMR ($\delta$, CDCl$_3$): 1.51 (m, 2H), 1.63 (m, 2H), 1.86 (m, 2H),$\delta$2.22 (s, 6H), 2.28 (m, 3H), 2.33 (s, 6H), 2.99 (m, 1H), 5.93 (s, 2H), 7.10 ($\delta$, J=8, 1H), 7.27 (m, 2H), 7.71 ($\delta$, J=8, 1H), 7.83 (t, J=8, 1H), 7.99 (m, 2H).

$^{13}$C-NMR ($\delta$, CDCl$_3$): 13.4, 20.3, 27.3, 28.2, 32.4, 42.8, 45.3, 71.8, 106.8, 118.0, 119.4, 126.7, 128.6, 129.4, 135.7, 138.4, 143.8, 151.5, 156.8.

MS (%): 374 (parent+1, 100).

More polar diastereomer, 10 mg (4%):

$^1$H-NMR ($\delta$, CDCl$_3$): 1.5–1.8 (m, 6H), 2.20 (s, 6H), 2.32 (s, 6H), 2.45 (dd, J=10,14, 1H), 2.60 (m, 2H), 2.95 (dd, J=5,13.5, 1H), 5.91 (s, 2H), 7.10 ($\delta$, J=8, 1H), 7.27 (m, 2H), 7.71 ($\delta$, J=8, 1H), 7.84 (t, J=8, 1H), 7.97 (m, 2H).

$^{13}$C-NMR ($\delta$, CDCl$_3$): 13.4, 23.5 27.5, 30.85, 41.0, 42.3, 43.3, 72.1, 106.8, 118.0, 119.5, 126.8, 128.6, 129.4, 136.0, 138.4, 142.7, 151.5, 156.7.

MS (%): 374 (parent+1, 100).

D. 6-[3-(2-Dimethylamino-cyclopentylmethyl)-phenyl]-pyridin-2-ylamine

To a 100 mL round-bottomed flask equipped with condenser and $N_2$ inlet were added 140 mg (0.375 mmol) 2-(2,5-dimethylpyrrolyl)-6-[3-(2-dimethylamino-cyclopentylmethyl)-phenyl]-pyridine, 9 mL ethanol, 1 mL water, and 261 mg (3.75 mmol) hydroxylamine hydrochloride. The reaction was refluxed 24 hours treated with additional hydroxylamine hydrochloride, and refluxed a further 12 hours. It was then cooled, poured into dilute aqueous hydrochloric acid, and washed with ethyl acetate. The aqueous layer was adjusted to pH 10 with 6N sodium hydroxide solution, and extracted with two portions of ethyl acetate. The combined organic layer was washed with brine, dried over sodium sulfate, and evaporated. The resulting oil (109 mg, 98.5%) was converted to the hydrochloride salt using 1N HCl in ether to afford 115 mg (83%) of a white solid, mp 60–80° C.

$^1$H-NMR ($\delta$, $CDCl_3$): 1.49 (m, 2H), 1.58 (m, 2H), 1.82 (m, 2H), 2.23 (m, 2H), 2.29 (s, 6H), 2.3 (m, 1H), 2.94 ($\delta$, J=9.6, 1H), 4.57 (bs, 2H), 6.38 ($\delta$, J=8, 1H), 7.20 (m, 2H), 7.43 (t, J=8, 1H), 7.80 (m, 2H).

$^{13}$C-NMR ($\delta$, $CDCl_3$): 20.3, 27.3, 28.2, 32.3, 42.8, 45.3, 71.9, 106.7, 110.6, 126.6, 129.2, 137.1, 138.2, 142.8, 156.2, 158.2.

MS (%): 296 (parent+1, 100).

EXAMPLE 12

6-[3-(2-(4-Methylpiperazin-1-yl)-cyclopentylmethyl)-phenyl]-pyridin-2-ylamine

Prepared as in Example 11, using N-methylpiperazine, to afford a 64% yield of the product as a mixture of diastereomers as the hydrochloride salt, mp 212–224° C.

$^1$H-NMR ($\delta$, $CDCl_3$): 1.44 (m, 2H), 1.51 (m, 2H), 1.7–1.8 (m, 2H), 2.21 (m, 2H), 2.25 (s, 6H), 2.3 (m, 1H), 2.4–2.6 (m, 8H), 2.88 (m, 1H), 4.60 (bs, 2H), 6.34 ($\delta$, J=8, 1H), 6.99 ($\delta$, J=8, 1H), 7.16 (m, 2H), 7.40 (t, J=8, 1H), 7.77 (m, 2H).

$^{13}$C-NMR ($\delta$, $CDCl_3$): 20.1, 27.3, 27.4, 32.5, 42.1, 46.0, 52.7, 55.1, 70.0, 106.7, 110.5, 126.6, 129.1, 137.0, 138.2, 142.8, 156.1, 158.2.

MS (%): 351 (parent+1, 100).

EXAMPLE 13

6-[4-(Piperidin-4-yl)-phenyl]-pyridin-2-ylamine

A. N-Benzyl-4-(4-bromophenyl)piperidine

To a 250 mL round-bottomed flask equipped with condenser and $N_2$ inlet were added 4.77 g (17.72 mmol) 3-(4-bromophenyl)glutaric anhydride (prepared as described in *J. Org. Chem.*, 21, 704 (1956)), 1.90 g (17.72 mmol) benzylamine, and 80 mL toluene. The reaction was refluxed 1.5 hours cooled, and concentrated. The residue was taken up in 80 mL acetic anhydride, and heated at 100° C. for 16 hours then cooled and evaporated several times with toluene to remove excess acetic anhydride. The residue was dissolved in 80 mL dry tetrahydrofuran and treated with 40 mL (80 mmol) of a 2 N solution of borane methyl sulfide in tetrahydrofuran. The reaction was refluxed 18 hours cooled, and evaporated, then dissolved in 80 mL ethanol and treated with 3.5 g sodium carbonate and 3.5 g cesium fluoride. The reaction was refluxed 16 hours cooled, and concentrated. The residue was taken up in water and ethyl acetate. The organic layer was separated, washed with brine, dried over sodium sulfate, and evaporated. The residue was chromatographed on silica gel using ethyl acetate/hexane as eluant to afford 2.94 g (50%) of an oil.

$^1$H-NMR ($\delta$, $CDCl_3$): 1.78 (m, 4H), 2.08 (m, 2H), 2.47 (m, 1H), 3.02 (m, 2H), 3.56 (s, 2H), 7.10 (d, J=8, 1H), 7.2–7.4 (m, 5H), 7.41 (d, J=8, 2H).

$^{13}$C-NMR ($\delta$, $CDCl_3$): 33.4, 42.2, 54.1, 63.5, 119.7, 127.0, 128.2, 128.7, 129.2, 131.4, 138.4, 145.5.

MS (%): 328/330 (parent, $Br^{79}/Br^{79}$, 15/19), 91 (100).

B. N-Benzyl4-(4-(2-(2,5-dimethylpyrrolyl)pyrid-6-yl)phenyl)piperidine

To a 125 mL three-necked round-bottomed flask equipped with septum and $N_2$ inlet were added 2.93 g (8.88 mmol) N-benzyl-4-(4-bromophenyl)piperidine and 30 mL dry ether. The solution was cooled to −70° C., and 6.66 mL (10.65 mmol) of a 1.6 N solution of butyl lithium in hexane added dropwise over 5 minutes. After stirring a further 5 minutes at −70° C., the solution was warmed slowly to room temperature over 25 minutes. A solution of 1.83 g (10.65 mmol) 2-(2,5-dimethylpyrrolyl)pyridine in 10 mL dry ether was then added dropwise over 5 minutes, and the reaction, which turned slowly dark red, stirred at room temperature for 3 hours. The reaction was quenched with aqueous ammonium chloride solution, partitioned between ethyl acetate and water, and the organic layer separated, washed with brine, and dried over sodium sulfate, allowing it to stand overnight to effect rearomatization of the pyridine ring. After evaporation of the solvent, the residue was chromatographed on silica gel using ethyl acetate/hexane followed by methanol/methylene chloride as eluant to afford 1.21 g (32%) of an oil.

$^1$H-NMR ($\delta$, $CDCl_3$): 1.86 (m, 4H), 2.16 (m, 2H), 2.23 (s, 6H), 2.58 (m, 1H), 3.05 (m, 2H), 3.59 (s, 2H), 5.95 (s, 2H), 7.12 (d, J=8, 1H), 7.2–7.4 (m, 7H), 7.73 (d, J=7, 1H), 7.85 (t, J=8, 1H), 8.03 (m, 2H).

$^{13}$C-NMR ($\delta$, $CDCl_3$): 13.5, 33.4, 42.5, 54.2, 63.5, 106.9, 118.1, 119.6, 127.1, 127.3, 128.2, 128.7, 129.3, 131.4, 136.3, 138.3, 138.5, 148.0, 151.7, 156.8.

MS (%): 422 (parent+1, 26), 91 (100).

C. 4-(4-(2-(2,5-Dimethylpyrrolyl)pyrid-6-yl)phenyl)piperidine

To a 100 mL round-bottomed flask equipped with condenser and $N_2$ inlet were added 1.21 g (2.87 mmol) N-benzyl-4-(4-(2-(2,5-dimethylpyrrolyl)pyrid-6-yl)phenyl)piperidine, 30 mL ethanol, 0.90 g (14.37 mmol) ammonium formate, and 140 mg 10% palladium-on-carbon (Pd-C). The reaction was refluxed 1 hour treated with additional ammonium formate and Pd-C, and refluxed 3 hours. It was then cooled and filtered through Celite with ethanol and methylene chloride. The filtrate was evaporated, taken up in ethyl acetate and aqueous sodium bicarbonate solution, and the organic layer separated, washed with brine, dried over sodium sulfate, and evaporated to afford 734 mg (77%) of an oil.

$^1$H-NMR ($\delta$, $CDCl_3$): 1.80 (m, 4H), 2.20 (s, 6H), 2.69 (m, 1H), 2.78 (m, 2H), 3.23 (m, 2H), 3.68 (bs, 1H), 5.92 (s, 2H), 7.10 (d, J=8, 1H), 7.32 (m, 2H), 7.71 (d, J=8, 1H), 7.84 (t, J=8, 1H), 8.01 (m, 2H).

$^{13}$C-NMR ($\delta$, $CDCl_3$): 13.5, 33.7, 42.5, 46.7, 106.9, 118.1, 119.6, 127.2, 128.5, 128.7, 136.4, 138.5, 147.7, 151.7, 156.8.

MS (%): 332 (parent+1, 100).

D. 6-[4-(Piperidin-4-yl)-phenyl]-pyridin-2-ylamine

To a 100 mL round-bottomed flask equipped with condenser and $N_2$ inlet were added 100 mg (0.302 mmol)

4-(4-(2-(2,5-dimethylpyrrolyl)pyrid-6-yl)phenyl)piperidine, 10 mL ethanol, 1 mL water, and 417 mg (6.04 mmol) hydroxylamine hydrochloride. The reaction was refluxed 20 hours cooled, and poured into dilute aqueous hydrochloric acid, then washed with ethyl acetate. The aqueous layer was adjusted to pH 10 with 6 N sodium hydroxide solution and extracted twice with ethyl acetate. The combined organic layer was washed with brine, dried over sodium sulfate, and evaporated. The resulting oil (77 mg, 100%) was converted to the hydrochloride salt using HCl in, ether to afford a tan solid, 32 mg (32%), mp dec. above 150° C.

$^1$H-NMR ($\delta$, CDCl$_3$): 1.63 (m, 2H), 1.80 (m, 2H), 2.60 (m, 1H), 2.68 (m, 2H), 3.14 (m, 2H), 4.68 (bs, 2H), 6.36 (d, J=8, 1H), 6.97 (d, J=7.5, 1H), 7.22 (m, 2H), 7.41 (t, J=8, 1H), 7.79 (m, 2H).

$^{13}$C-NMR ($\delta$, CDCl$_3$): 34.1, 42.5, 46.8, 106.9, 110.5, 126.9, 128.3, 137.6, 138.2, 147.0, 155.9, 158.3.

MS (%): 254 (parent+1, 100).

EXAMPLE 14

6-[3-(2-(N-Cyclohexylamino)-cyclopentylmethyl)-phenyl]-pyridin-2-ylamine

Prepared as in Example 11, using cyclohexylamine, to afford a 76% yield of the less polar isomer after separation of isomers, assigned the cis stereochemistry, as the hydrochloride salt, mp 198–205° C.

$^1$H-NMR ($\delta$, CDCl$_3$): 1.0–1.9 (m, 16H), 2.21 (m, 1H), 2.34 (m, 1H), 2.45 (m, 1H), 2.82 (dd, J=5,13, 1H, assigned cis stereochemistry), 3.21 (m, 1H), 4.52 (broad s, 2H, NH$_2$), 6.40 (d, J=8, 1H), 7.04 (d, J=8, 1H), 7.23 (m, 2H), 7.45 (t, J=8, 1H), 7.81 (m, 2H).

$^{13}$C-NMR ($\delta$, CDCl$_3$): 20.6, 25.2, 26.1, 28.3, 31.1, 33.9, 34.1, 43.8, 54.9, 58.3, 106.7, 110.6, 126.6, 129.1, 137.0, 138.2, 142.7, 156.2, 158.1.

MS (%): 350 (parent+1, 100).

Anal. Calc'd. for C$_{23}$H$_{31}$N$_3$.2HCl.H$_2$O: C, 62.72; H, 8.01; N, 9.54. Found: C, 62.66; H, 8.12; N, 8.83.

EXAMPLE 15

6-[3-(2-(N-Cyclohexylamino)-cyclopentylmethyl)-phenyl]-pyridin-2-ylamine

Prepared as in Example 11, using cyclohexylamine, to afford a 85% yield of the more polar isomer after separation of isomers, assigned the trans stereochemistry, as the hydrochloride salt, mp 175–185° C.

$^1$H-NMR ($\delta$, CDCl$_3$): 0.9–1.4 (m, 6H), 1.5–2.0 (m, 11H), 2.33 (m, 1H), 2.52 (dd, J=8.5,13, 1H assigned trans stereochemistry), 2.81 (m, 2H), 4.56 (broad s, 2H, NH$_2$), 6.38 (d, J=8, 1H), 7.02 (d, J=8, 1H), 7.21 (m, 2H), 7.43 (t, J=8, 1H), 7.79 (m, 2H).

$^{13}$C-NMR ($\delta$, CDCl$_3$): 22.5, 25.1, 25.2, 26.0, 30.7, 33.3, 33.6, 34.5, 40.3, 48.0, 55.2, 61.6, 106.7, 110.6, 126.6, 129.1, 137.2, 138.2, 141.9, 156.1, 158.2.

MS (%): 350 (parent+1, 100).

Anal. Calc'd. for C$_{23}$H$_{31}$N$_3$.2HCl.3/2H$_2$O: C, 61.46; H, 8.07; N, 9.35. Found: C, 61.78; H, 8.01; N, 9.12.

EXAMPLE 16

6-[3-(2-(N-Phenethylamino)-cyclopentylmethyl)-phenyl]-pyridin-2-ylamine

Prepared as in Example 11, using phenethylamine, to afford a 85% yield of the less polar isomer after separation of isomers, assigned the cis stereochemistry, as the hydrochloride salt, mp 170–185° C.

$^1$H-NMR ($\delta$, CDCl$_3$): 1.52 (m, 6H), 1.75 (m, 2H), 2.20 (m, 1H), 2.36 (dd, J=10,13, 1H), 2.7–3.0 (m, 4H), 4.53 (broad s, 2H, NH$_2$), 6.41 (d, J=8, 1H), 7.04 (d, J=8, 1H), 7.14 (m, 2H), 7.2–7.3 (m, 5H), 7.46 (t, J=8, 1H), 7.79 (m, 2H).

$^{13}$C-NMR ($\delta$, CDCl$_3$): 21.2, 28.9, 30.7, 34.2, 36.7, 44.6, 49.9, 61.7, 106.9, 110.8, 126.3, 126.8, 128.6, 128.9, 139.1, 137.3, 138.4, 140.4, 142.7, 156.3, 158.3.

MS (%): 372 (parent+1, 100).

Anal. Calc'd for C$_{25}$H$_{29}$N$_3$.2HCl.5/3H$_2$O: C, 63.29; H, 7.29; N, 8.86. Found: C, 63.31; H, 7.35; N, 8.66.

EXAMPLE 17

6-[3-(2-(N-Phenethylamino)-cyclopentylmethyl)-phenyl]-pyridin-2-ylamine

Prepared as in Example 11, using phenethylamine, to afford a 85% yield of the more polar isomer after separation of isomers, assigned the trans stereochemistry, as the hydrochloride salt, mp 110–130° C.

$^1$H-NMR ($\delta$, CDCl$_3$): 1.29 (m, 2H), 1.40 (m, 1H), 1.59 (m, 2H), 1.75 (m, 1H), 1.93 (m, 2H), 2.51 (dd, J=8.5,13, 1H), 2.6–2.8 (m, 5H), 4.55 (broad s, 2H, NH$_2$), 6.40 (d, J=8, 1H), 7.05 (d, J=8, 1H), 7.2–7.4 (m, 7H), 7.46 (t, J=8, 1H), 7.81 (m, 2H).

$^{13}$C-NMR ($\delta$, CDCl$_3$): 22.5, 30.8, 32.6, 36.4, 40.3, 47.6, 49.70, 64.5, 106.8, 110.6, 126.0, 126.6, 128.3, 128.6, 129.0, 137.25, 138.2, 140.0, 141.8, 156.0, 158.2.

MS (%): 372 (parent+1, 100).

Anal. Calc'd for C$_{25}$H$_{29}$N$_3$.2HCl.3/2H$_2$O: C, 63.69; H, 7.27; N, 8.91. Found: C, 63.80; H, 7.41; N, 8.53.

EXAMPLE 18

6-[3-(2-(4-Methylpiperazin-1-yl)-cyclohexylmethyl)-phenyl]-pyridin-2-ylamine

Prepared as in Example 11, using N-methylpiperazine, to afford a 96% yield of the product as a mixture of diastereomers as the hydrochloride salt, mp 195–208° C.

$^1$H-NMR ($\delta$, CDCl$_3$): 1.1–1.6 (m, 8H), 1.8–1.9 (m, 3H), 2.27 (s, 3H), 2.4–2.7 (m, 8H), 2.90 (m, 1H), 4.53 (broad s, 2H, NH$_2$), 6.40 (d, J=8, 1H), 7.02 (d, J=8, 1H), 7.18 (m, 2H), 7.45 (t, J=8, 1H), 7.79 (m, 2H).

$^{13}$C-NMR ($\delta$, CDCl$_3$): 13.8, 24.5, 25.7, 26.9, 30.5, 37.2, 45.9, 50.1, 55.5, 65.8, 106.7, 110.6, 126.6, 129.1, 137.0, 138.2, 143.1, 156.2, 158.1.

MS (%): 365 (parent+1, 100).

Anal. Calc'd for C$_{23}$H$_{32}$N$_4$.3HCl.5/2H$_2$O.2/3(C$_4$H$_{10}$O): C, 57.26; H, 8.11; N, 10.41. Found: C, 57.15; H, 7.81; N, 10.11.

EXAMPLE 19

6-[3-(2-(N-benzylamino)-cyclohexylmethyl)-phenyl]-pyridin-2-ylamine

Prepared as in Example 11, using benzylamine, to afford a 72% yield of the product as a mixture of diastereomers as the hydrochloride salt, mp 170–1 85° C.

$^1$H-NMR ($\delta$, CDCl$_3$): 1.3–1.4 (m, 4H), 1.6–1.8 (m, 4H), 2.57 (dd, J=9,13, 2H), 2.73 (m, 1H), 2.84 (m, 1H), 3.77 (dd, J=9,38, 2H), 4.58 (broad s, 2H, NH$_2$), 6.40 (d, J=8, 1H), 7.05 (d, J=8, 1H), 7.2–7.4 (m, 7H), 7.46 (t, J=8, 1H), 7.82 (m, 2H).

$^{13}$C-NMR (δ, CDCl$_3$): 25.2, 25.6, 27.0, 28.6, 39.0, 50.8, 51.3, 56.1, 60.1, 106.7, 110.6, 126.5, 126.6, 128.1, 128.3, 129.5, 137.1, 138.3, 141.2, 141.9, 142.5, 156.2, 158.2.

MS (%): 372 (parent+1, 100).

Anal. Calc'd for C$_{25}$H$_{29}$N$_3$.2HCl.3/2H$_2$O: C, 63.69; H, 7.27; N, 8.91. Found: C, 64.03; H, 7.25; N, 8.90.

EXAMPLE 20

6-{4-[2-(2-Ethoxy-ethylamino)-cyclohexylmethyl]-phenyl}-pyridin-2-ylamine

Prepared as in Example 11, using 2-ethoxyethylamine, to afford a 100% yield of the product as a mixture of diastereomers as the hydrochloride salt, mp 70–90° C.

$^1$H-NMR (δ, CDCl$_3$): 1.21 (t, J=8, 3H), 1.2–1.7 (m, 8H), 2.5–2.9 (multiplets, 3H), 3.4–3.6 (m, 7H), 4.54 (broad s, 2H, NH$_2$), 6.39 (d, J=8, 1H), 7.03 (d, J=7.5, 1H), 7.22 (m, 2), 7.44 (t, J=8, 1H), 7.80 (m, 2H).

$^{13}$C-NMR (δ, CDCl$_3$): 15.2, 26.9, 28.7, 30.4, 32.2, 46.2, 46.8, 57.0, 60.5, 66.25, 70.1, 106.7, 110.6, 126.5, 129.3, 167.0, 138.2, 141.6, 142.4, 156.2, 158.2.

MS (%): 354 (parent+1, 100).

Anal. Calc'd for C$_{22}$H$_{31}$N$_3$O.2HCl.9H$_2$O: C, 44.90; H, 8.73; N, 7.14. Found: C, 44.69; H, 8.82; N, 6.82.

EXAMPLE 21

6-[4-(2-(4-Benzylpiperazin-1-yl)-cyclohexylmethyl)-phenyl]-pyridin-2-ylamine

Prepared as in Example 11, using N-benzylpiperazine, to afford a 67% yield of the product as a mixture of diastereomers as the hydrochloride salt, mp 205–215° C.

$^1$H-NMR (δ, CDCl$_3$): 1.0–1.8 (m, 8H), 1.8–1.9 (m, 3H), 2.4–2.6 (m, 8H), 2.92 (m, 1H), 3.51 (singlets, 2H), 4.53 (bs, 2H, NH$_2$), 6.40 (d, J=8, 1H), 7.03 (d, J=7, 1H), 7.1–7.3 (m, 7H), 7.45 (t, J=7.5, 1H), 7.79 (m, 2H).

$^{13}$C-NMR (δ, CDCl$_3$): 19.8, 24.5, 25.7, 26.9, 30.5, 37.2, 50.1, 53.0, 53.5, 63.1, 65.9, 106.7, 110.6, 126.6, 126.9, 128.1, 129.1, 129.2, 137.0, 138.0, 138.2, 143.1, 156.2, 158.1.

MS (%): 441 (parent+1, 100).

Anal. Calc'd for C$_{29}$H$_{36}$N$_4$.3HCl.3/2H$_2$O: C, 60.36; H, 7.34; N, 9.71. Found: C, 60.53; H, 7.35; N, 8.97.

EXAMPLE 22

6-[4-(2-(4-(N-lsopropylacetamido)piperazin-1-yl)-cyclohexylmethyl)-phenyl]-pyridin-2-ylamine Prepared as in Example 11, using N-(N-isopropylacetamido)piperazine, to afford a 94% yield of the product as a mixture of diastereomers as the hydrochloride salt, mp 180–200° C. (dec.).

$^1$H-NMR (δ, CDCl$_3$): 1.147 and 1.148 (doublets, J=6, 6H), 1.2–1.8 (m, 11H), 2.6 (broad m, 8H), 2.95 (s, 2H), 4.088 and 4.092 (heptets, J=6, 1H), 4.53 (broad s, 2H, NH$_2$), 6.40 (d, J=8, 1H), 7.02 (d, J=8, 1H), 7.17 (m, 2H), 7.45 (t, J=8, 1H), 7.79 (m, 2H).

$^{13}$C-NMR (δ, CDCl$_3$): 22.75, 24.5, 25.7, 26.1, 30.6, 60.5, 50.2, 53.8, 61.5, 65.8, 106.7, 110.6, 126.6, 129.1, 137.0, 138.2, 143.0, 156.1, 158.2, 169.2.

MS (%): 450 (parent+1, 100).

Anal. Calc'd for C$_{27}$H$_{39}$N$_5$O.3HCl.1/2H$_2$O(C$_4$H$_{10}$O): C, 57.98; H, 8.32; N, 10.91. Found: C, 57.77; H, 7.90; N, 10.85.

EXAMPLE 23

6-[4-((2-(Phenethyl)-[2.2.1]bicyclohept-1-yl)methyl)-phenyl]-pyridin-2-ylamine

Prepared as in Example 11, using N-phenethylamine, to afford a 73% yield of the product assigned the trans stereochemistry, mp 195–204° C. (dec.).

$^1$H-NMR (δ, CDCl$_3$): 1.2–1.4 (m, 4H), 1.58 (m, 2H), 1.94 (broad s, 1H), 2.27 (m, 1H), 2.33 (broad s, 1H), 2.4904 (dd, J=10,14, 2H), 2.7–2.8 (m, 4H), 3.10 (dd, J=4,11, 1H, assigned trans stereochemistry), 4.54 (bs, 2H, NH$_2$), 6.41 (d, J=8, 1H), 7.04 (d, J=7, 1H), 7.2–7.3 (m, 5H), 7.27 (m, 2H), 7.46 (t, J=8, 1H), 7.79 (m, 2H).

$^{13}$C-NMR (δ, CDCl$_3$): 20.3, 22.4, 31.7, 36.6, 37.3, 39.9, 40.7, 43.3, 50.1, 59.3, 106.8, 110.7, 126.1, 126.7, 128.4, 128.7, 128.9, 137.1, 138.3, 140.4, 142.8, 156.2, 158.2.

MS (%): 398 (parent+1, 100).

Anal. Calc'd for C$_{27}$H$_{31}$N$_3$.2HCl.H$_2$O: C, 66.39; H, 7.22; N, 8.60. Found: C, 66.00; H, 7.22; N, 8.60.

EXAMPLE 24

6-[4-((2-(3-aza-bicyclo[3.1.0]hex-6-ylamino)-[2.2.1]bicyclohept-1-yl)methyl)-phenyl]-pyridin-2-ylamine Prepared as in Example 11, using 3-aza-bicyclo[3.1.0]hex-6-ylamine, to afford a 78% yield of the product as a mixture of diastereomers as the hydrochloride salt, mp 248–260° C. (dec.).

$^1$H-NMR (δ, CDCl$_3$): 1.04 (broad d, J=9, 2H), 1.29 (m, 4H), 1.53 (m, 2H), 1.59 (broad s, 1H), 1.89 (broad s, 1H), 2.12 (m, 1H), 2.21 (ddd, J=3,14, 24, 2H), 2.48 (broad s, 1H), 2.78 (dd, J=4,13, 1H assigned trans stereochemistry), 3.02 (m, 4H), 4.55 (broad s, 2H, NH$_2$), 6.39 (d, J=8, 1H), 7.02 (d, J=7.5, 1H), 7.19 (m, 2H), 7.44 (t, J=8, 1H), 7.79 (m, 2H).

$^{13}$C-NMR (δ, CDCl$_3$): 22.4, 25.5, 25.6, 27.35, 32.5, 36.3, 36.8, 38.3, 41.3, 49.5, 52.6, 53.6, 106.8, 110.6, 126.7, 128.9, 137.1, 138.3, 142.5, 156.2, 158.3.

MS (%): 375 (parent+1, 100).

Anal. Calc'd for C$_{24}$H$_{30}$N$_4$.3HCl.1/2H$_2$O.1/2(C$_4$H$_{10}$O): C, 58.92; H, 7.42; N, 10.57. Found: C, 59.02; H, 7.50; N, 10.64.

EXAMPLE 25

6-[2-(N-Phenethylamino)-5-phenyl-cyclohexylmethyl)methyl)-phenyl]-pyridin-2-ylamine Prepared as in Example 11, using N-phenethylamine, to afford a 77.5% yield of the product as a mixture of diastereomers as the hydrochloride salt, mp 178–192° C. (dec.).

$^1$H-NMR (δ, CDCl$_3$): 1.2–1.5 (m, 6H), 2.2–2.5 (m, 3H), 2.84 (m, 4H), 3.03 (m, 1H), 3.13 (m, 1H), 4.49 (broad s, 2H, NH$_2$), 6.41 (d, J=8, 1H), 7.02 (d, J=7.5 (1H), 7.2–7.4 (m, 12H), 7.46 (t, J=8, 1H), 7.74 (m, 2H).

$^{13}$C-NMR (δ, CDCl$_3$): 32.6, 33.0, 36.7, 338.7, 38.8, 43.8, 44.7, 48.1, 60.4, 106.8, 110.8, 125.9, 126.3, 126.6, 126.8, 128.3, 128.5, 128.8, 129.6, 137.3, 138.3, 140.1, 141.0, 146.8, 156.2, 158.2.

MS (%): 462 (parent+1, 100).

Anal. Calc'd for C$_{32}$H$_{35}$N$_3$.2HCl.1/2CH$_2$Cl$_2$.(C$_4$H$_{10}$O): C, 66.41; H, 7.48; N, 6.37. Found: C, 66.42; H, 7.29; N, 6.17.

EXAMPLE 26

6-[4-((2-(Phenethylamino)-[2.2.1]bicyclohept-1-yl)methyl)-phenyl]-pyridin-2-ylamine Prepared as in Example 11, using N-phenethylamine, to afford a 96% yield of the product assigned the cis stereochemistry, mp 170–180° C. (dec.).

¹H-NMR (δ, CDCl₃): 1.08 (m, 1H), 1.15 (m, 1H), 1.2–1.4 (m, 4H), 1.57 (m, 2H), 1.68 (m, 1H), 2.0–2.2 (m, 2H), 2.61 (m, 1H), 2.69 (m, 4H), 2.77 (m, 1H), 4.50 (broad s, 2H, NH₂), 6.42 (d, J=8, 1H), 7.05 (d, J=8, 1H), 7.12 (m, 2H), 7.22 (m, 5H), 7.47 (t, J=8,1 H), 7.81 (m, 2H).

¹³C-NMR (δ, CDCl₃): 22.1, 27.4, 36.4, 36.6, 37.1, 39.0, 41.7, 49.7, 52.5, 68.5, 106.8, 110.7, 126.0, 126.7, 128.4, 128.6, 128.9, 137.3, 138.3, 140.1, 142.3, 156.1, 158.2.

MS (%): 398 (parent+1, 100).

Anal. Calc'd for C₂₇H₃₁N₃.2HCl.H₂O.1/2(C₄H₁₀O): C, 66.28; H, 7.67; N, 8.00. Found: C, 66.57; H, 7.41; N, 7.64.

EXAMPLE 27

6-[((2-(3-aza-bicyclo[3.1.0]hex-6-ylamino)-5-phenyl-cyclohexylmethyl)methyl)-phenyl]-pyridin-2-ylamine Prepared as in Example 11, using 3-aza-bicyclo[3.1.0]hex-6-ylamino, to afford a 56% yield of the product as a mixture of diastereomers as the hydrochloride salt, mp 200–220° C. (dec.).

¹H-NMR (δ, CDCl₃): 1.2–3.2 (multiplets for 18H), 4.53 and 4.58 (broad singlets, 2H, NH₂), 6.40 and 6.44 (doublets, J=8, 1H), 7.02 and 7.05 (doublets, J=7.5, 1H), 7.16 (m, 2H), 7.25 (m, 5H), 7.40 and 7.45 (triplets, J=8, 1H), 7.89 and 7.87 (multiplets, 2H).

¹³C-NMR (δ, CDCl₃): 25.3, 26.1, 30.9, 32.9, 34.6, 37.1, 39.9, 53.0, 64.9, 66.5, 106.8, 107.2, 110.8, 110.9, 125.9, 126.8, 127.0, 127.1, 128.3, 129.2, 138.4, 138.5, 156.2, 158.2.

MS (%): 439 (parent+1, 100).

EXAMPLE 28

N-Methyl-(2-aminopyrid-6-yl-benzylidene)-oxindole

Prepared as in Example 11, using N-methyloxindole, to afford a 100% yield of the product as a mixture of diastereomers as the hydrochloride salt, mp 170–175° C. (dec.).

¹H-NMR (δ, CDCl₃): 3.26 (s, 3H), 4.60 (broad s, 2H, NH₂), 6.47 (d, J=8, 1H), 6.80 (d, J=8, 1H), 6.86 (t, J=8, 1H), 7.12 (d, J=8, 1H), 7.24 (m, 1H), 7.50 (t, J=8, 1H), 7.70 (m, 2H), 7.85 (s, 1H), 8.02 (m, 2H).

¹³C-NMR (δ, CDCl₃): 26.1, 107.7, 108.1, 110.9, 121.1, 121.7, 122.8 126.8, 127.1, 129.7, 132.3, 135.0, 136.7, 138.4, 140.6, 144.1, 154.9, 158.3, 168.45.

MS (%): 328 (parent+1, 100).

Anal. Calc'd for C₂₁H₁₇N₃O.1/4H₂O: C, 76.00; H, 5.31; N, 12.66. Found: C, 75.93; H, 5.30; N, 11.87.

EXAMPLE 29

N-Methyl-(2-aminopyrid-6-yl-benzyl)-oxindole

Prepared by reduction of Example 28, to afford a 60% yield of the product as a mixture of diastereomers as the hydrochloride salt, mp 45–55° C. (dec.).

¹H-NMR (δ, CDCl₃): 2.91 (dd, J=10,14, 1H), 3.14 (s, 3H), 3.52 (dd, J=4,14, 1H), 3.73 (m, 1H), 4.53 (broad s, 2H, NH₂), 6.42 (d, J=8, 1H), 6.725 (d, J=8, 1H), 6.80 (m 1H), 6.88 (t, J=7.5, 1H), 7.05 (d, J=8, 1H), 7.21 (m, 3H), 7.46 (t, J=7.5, 1H), 7.81 (m, 2H).

¹³C-NMR (δ, CDCl₃): 26.1, 36.5, 47.0, 107.0, 107.9, 110.7, 122.1, 124.6, 126.7, 127.9, 129.6, 138.0, 138.3, 138.5, 144.2, 155.7, 158.3, 177.0.

MS (%): 330 (parent+1, 100).

EXAMPLE 30

N-(2-Dimethylaminoethyl)-(2-aminopyrid-6-yl-benzylidene)-oxindole

Prepared as in Example 28, using N-(2-dimethylaminoethyl)oxindole, to afford a 91% yield of the product as a mixture of diastereomers as the hydrochloride salt, mp 165–190° C. (dec.).

¹H-NMR (δ, CDCl₃): 2.33 (s, 6H), 2.59 (t, J=7, 2H), 3.90 (t, J=7, 2H), 4.55 (broad s, 2H, NH₂), 6.48 (d, J=8, 1H), 6.85 (m, 2H), 7.14 (d, J=7.5, 1H), 7.24 (m, 2H), 7.51 (t, J=8, 1H), 7.71 (m, 2H), 7.85 (s, 1H), 8.02 (m, 2H).

¹³C-NMR (δ, CDCl₃): 37.6, 45.1, 55.6, 107.0, 107.7, 110.4, 121.1, 122.4, 125.9, 126.2, 129.1, 131.7, 136.3, 137.8, 157.6. Not all carbons were visible in this scan due to limited compound solubility.

MS (%): 385 (parent+1, 100).

Anal. Calc'd for C₂₄H₂₄N₄O.2HCl.H₂O: C, 60.63; H, 5.94; N, 11.78. Found: C, 60.61; H, 6.13; N, 10.12.

EXAMPLE 31

N-(2-Dimethylaminoethyl)-(2-aminopyrid-6-yl-benzyl)-oxindole

Prepared by reduction of Example 30 using palladium-catalyzed ammonium formate, to afford a 97% yield of the product as a mixture of diastereomers as the hydrochloride salt, mp 120–135° C. (dec.).

¹H-NMR (δ, CDCl₃): 2.25 (s, 6H), 2.39 9m, 2H), 2.95 (dd, J=9,14, 1H), 3.48 (dd, J=4,14, 1H), 3.7–3.9 (m, 3H), 4.47 (broad s, 2H, NH₂), 6.42 (d, J=8, 1H), 7.76 (d, J=8, 1H), 6.84 (m, 1H), 6.89 (t, J=7, 1H), 7.05 (d, J=7.5, 1H), 7.18 (m, 2H), 7.25 (m, 1H), 7.46 (t, J=8, 1H), 7.79 (m, 2H).

¹³C-NMR (δ, CDCl₃): 36.5, 38.2, 45.6, 46.9, 55.9, 107.0, 108.1, 110.7, 122.0, 124.7, 126.6, 127.9, 128.4, 129.7, 130.9, 138.0, 138.3, 143.5, 155.8, 158.2, 176.8.

MS (%): 387 (parent+1, 100).

EXAMPLE 32

6-[(N-5-lsoxazolylmethyl)-4-(piperidin-4-yl)-phenyl]-pyridin-2-ylamine

Prepared from Example 13, using 5-bromomethylisoxazole to alkylate 6-[4-(piperidin-4-yl)-4-yl)-phenyl]-pyridin-2-ylamine, in ethyl acetate, in 90%, mp 122–127° C.

¹H-NMR (δ, CDCl₃): 1.81 (m, 4H), 2.18 (m, 2H), 2.485 (m, 1H), 3.00 (m, 2H), 3.735 (s, 2H), 4.57 (broad s, 2H, NH₂), 6.17 (d, J=1.5, 1H), 6.38 (d, J=8, 1H), 7.01 (d, J=8, 1H), 7.24 (m, 2H), 7.43 (t, J=8, 1H), 7.81 (m, 2H), 8.18 (d, J=1.7, 1H).

¹³C-NMR (δ, CDCl₃): 33.2, 41.8, 53.4, 53.9, 102.4, 106.8, 110.6, 126.8, 126.9, 137.7, 138.2, 146.4, 150.1, 155.9, 158.2, 168.9.

MS (%): 335 (parent+1, 100).

Anal. Calc'd for C₂₀H₂₂N₄O.1/4(C₄H₈O₂): C, 70.76; H, 6.79; N, 15.72. Found: C, 70, 83; H, 6.62; N, 15.73.

EXAMPLE 33

6-[(N-Acetamido)-4-(piperidin-4-yl)-phenyl]-pyridin-2-ylamine

Prepared from Example 13, using iodoacetamide to alkylate 6-[4-(piperidin-4-yl)-phenyl]-pyridin-2-ylamine, in 55%, mp 224–227° C.

¹H-NMR (δ, DMSO-d₆): 1.76 (m, 2H), 2.17 (m, 1H), 2.51 (m, 2H), 2.88 (s, 2H), 2.91 (m, 4H), 5.94 (d, J=4.5, 1H), 6.39 (d, J=8, 1H), 7.01 (d, J=7, 1H), 7.19 (m, 1H), 7.30 (m, 2H), 7.44 (t, J=8, 1H), 7.90 (m, 2H).

¹³C-NMR (δ, DMSO-d₆): 33.0, 41.1, 54.0, 61.7, 106.7, 108.0, 126.3, 126.8, 137.3, 137.9, 146.5, 154.3, 159.4, 172.0.

MS (%): 311 (parent+1, 100).

Anal. Calc'd for $C_{18}H_{22}N_4O.1/2H_2O$: C, 67.69; H, 7.26; N, 17.54. Found: C, 67.96; H, 7.03; N, 17.37.

EXAMPLE 34

6-[(N-Benzoylmethyl)-4-(piperidin-4-yl)-phenyl]-pyridin-2-ylamine

Prepared from Example 13, using phenacyl bromide to alkylate 6-[4-(piperidin-4-yl)-phenyl]-pyridin-2-ylamine, in 75%, mp 180–200° C. as the hydrochloride salt.

¹H-NMR (δ, CDCl₃): 1.8–2.0 (m, 4H), 2.27 (m, 2H), 2.55 (m, 1H), 3.12 (m, 2H), 3.85 (s, 2H), 4.57 (broad s, 2H, NH₂), 6.40 (d, J=8, 1H), 7.03 (d, J=7.5, 1H), 7.28 (m, 2H), 7.45 (m, 3H), 7.55 (t, J=7.5, 1H), 7.83 (m, 2H), 8.01 (m, 2H).

¹³C-NMR (δ, CDCl₁₃): 33.2, 42.0, 54.6, 64.8, 106.8, 110.6, 126.8, 127.0, 128.1, 128.5, 133.1, 136.1, 137.6, 138.3, 146.7, 155.9, 158.1, 196.7.

MS (%): 372 (parent+1, 100). Anal. Calc'd for $C_{24}H_{25}N_3O.2HCl.3/4H_2O$: C, 62.95; H, 6.27; N, 9.18. Found: C, 63.13; H, 6.38; N, 9.07.

EXAMPLE 35

6-[(N-(3,4-Dimethoxybenzyl))-4-(piperidin-4-yl)-phenyl]-pyridin-2-ylamine

Prepared from Example 13, using 3,4-dimethoxybenzyl bromide to alkylate 6-[4-(piperidin-4-yl)-phenyl]-pyridin-2-ylamine, in 89%, mp 150–165° C. as the hydrochloride salt.

¹H-NMR (δ, CDCl₃): 1.85 (m, 4H), 2.18 (m, 2H), 2.54 (m, 1H), 3.06 (m, 2H), 3.56 (s, 2H), 3.86 (s, 3H), 3.89 (s, 3H), 4.6 (broad s, 2H), 6.40 (d, J=8, 1H), 6.82 (m, 2H), 6.95 (m, 1H), 7.02 (d, J=7.5, 1H), 7.27 (m, 2H), 7.45 (t, J=8, 1H), 7.82 (m, 2H).

¹³C-NMR (δ, CDCl₃): 32.9, 42.2, 53.8, 55.91, 55.935, 60.4, 62.8, 106.9, 1110.7, 110.8, 112.6, 121.7, 126.9, 127.1, 137.7, 138.3, 146.6, 148.3, 156.1, 158.3.

MS (%): 404 (parent+1, 100).

Anal. Calc'd for $C_{25}H_{29}N_3O_2.2HCl.7/4H_2O$: C, 59.11; H, 6.85; N, 8.27. Found: C, 59.19; H, 6.92; N, 8.21.

EXAMPLE 36

6-[(N-(3,4-Methylenedioxybenzyl))-4-(piperidin-4-yl)-phenyl]-pyridin-2-ylamine

Prepared from Example 13, using 3,4-methylenedioxybenzyl bromide to alkylate 6-[4-(piperidin-4-yl)-phenyl]-pyridin-2-ylamine, in 82%, mp 150–165° C. as the hydrochloride salt.

¹H-NMR (δ, CDCl₃): 1.87 (m, 4H), 2.11 (m, 2H), 2.53 (m, 1H), 3.05 (m, 2H), 3.51 (s, 2H), 5.94 (s, 2H), 6.41 (d, J=8, 1H), 6.76 (m, 2H), 6.89 (s, 1H), 7.02 (d, J=7.5, 1H), 7.27 (m, 2H), 7.46 (t, J=8, 1H), 7.83 (m, 2H).

¹³C-NMR (δ, CDCl₃):33.0, 42.2, 53.8, 62.8, 100.9, 106.9, 107.9, 109.8, 110.7, 122.6, 126.9, 127.1, 131.4, 137.7, 138.4, 146.7, 147.6, 156.1, 158.3.

MS (%): 388 (parent+1, 100).

Anal. Calc'd for $C_{24}H_{25}N_3O_2.3/2H_2O.2HCl$: C, 59.14; H, 6.20; N, 8.62. Found: C, 59, 22; H, 6.32; N, 8.53.

EXAMPLE 37

6-[(N-(2-Furyl)methyl)-4-(piperidin-4-yl)-phenyl]-pyridin-2-ylamine

Prepared from Example 13, using furfuryl bromide to alkylate 6-[4-(piperidin-4-yl)-phenyl]-pyridin-2-ylamine, in 100%, mp 75–95° C. as the hydrochloride salt.

¹H-NMR (δ, CDCl₃): 1.8–1.9 (m, 4H), 2.11 (m, 2H), 2.49 (m, 1H), 3.02 (m, 2H), 3.56 (s, 2H), 4.6 (broad s, 2H, NH₂), 6.21 (m, 1H), 6.30 (m, 1H), 6.38 (d, J=8, 1H), 7.00 (d, J=7.5, 1H), 7.25 (m, 2H), 7.37 (m, 1H), 7.43 (t, J=7.5, 1H), 7.80 (m, 2H).

¹³C-NMR (δ, CDCl₃): 33.1, 42.1, 53.8, 55.0, 136.8 128.8, 110.0, 110.6 126.8, 127.0, 137.6, 138.2, 142.1, 146.7, 151.6, 156.0, 158.2.

MS (%): 334 (parent+1, 100).

Anal. Calc'd for $C_{21}H_{23}N_3O.2HCl.3/4H_2O$: C, 57.60; H, 6.56; N, 9.60. Found: C, 57.66; H, 6.69; N, 9.47.

EXAMPLE 38

N-[4'-(6-Amino-pyridin-2-yl)-biphenyl-4-ylmethyl]-5,6-dimethoxy-1,2,3,4-tetrahydroisoquinoline Prepared as in Example 2, using 5,6-dimethoxy-1,2,3,4-tetrahydroisoquinoline for the reductive amination step, with a 88% yield for the final deblocking, mp 205–209° C.:

¹H-NMR (δ, CDCl₃): 2.72 (m, 2H), 2.77 (m, 2H), 3.52 (s, 2H), 3.66 (s, 2H), 3.72 (s, 3H), 3.75 (s, 3H), 3.8 (broad s, 2H), 6.39 (d, J=8, 1H), 6.43 (s, 1H), 6.53 (s, 1H), 6.98 (d, J=7.5, 1H), 7.3–7.4 (m, 3H), 7.5–7.7 (m, 4H), 7.85 (m, 2H).

¹³C-NMR (δ, CDCl₃: 28.2, 50.6, 55.4, 55.8, 62.2, 107.5, 139.5, 110.9, 111.4, 125.9, 126.1, 126.9, 127.0, 127.3, 129.9, 136.7, 138.5, 138.6, 140.9, 147.2, 147.5, 155.5, 158.6.

MS (%): 452 (parent+1, 100).

Anal. Calc'd for $C_{29}H_{29}N_3O_2.1/2H_2O$: C, 75.63; H, 6.57; N, 9.12. Found: C, 75.75; H, 6.37; N, 9.20.

EXAMPLE 39

6-[(N-(5-lsothiazolyl)methyl)-4-(piperidin-4-yl)-phenyl]-pyridin-2-ylamine

Prepared from Example 13, using 5-isothiazolyl bromide to alkylate 6-[4-(piperidin-4-yl)-phenyl]-pyridin-2-ylamine, in 95%, mp 140–145° C.

¹H-NMR (δ, CDCl₃): 1.795 (m, 4H), 2.16 (m, 2H), 2.49 (m, 1H), 3.02 (m, 4H), 3.835 (s, 2H), 6.385 (d, J=8, 1H), 6.96 (d, J=7.5, 1H), 7.06 (s, 1H), 7.24 (m, 2H), 7.42 (t, J=8, 1H), 7.75 (m, 2H), 8.35 (s, 1H).

¹³C-NMR (δ, CDCl₃): 33.1, 41.9, 54.1, 55.4, 107.1, 110.75, 122.2, 126.9, 127.0, 1337.6, 138.4, 146.5, 155.9, 157.4, 158.3, 166.6.

MS (%): 351 (parent+1, 100).

Anal. Calc'd for $C_{20}H_{22}N_4S.1/2H_2O$: C, 66.82; H, 6.45; N, 15.58. Found: C, 67.08; H, 6.51; N, 15.23.

EXAMPLE 40

6-[(N-(5-Thiazolyl)methyl)-4-(piperidin-4-yl)-phenyl]-pyridin-2-ylamine

Prepared from Example 13, using 5-thiazolyl bromide to alkylate 6-[4-(piperidin-4-yl)-phenyl]-pyridin-2-ylamine, in 99%, mp 151–154° C.

¹H-NMR (δ, CDCl₃): 1.81 (m, 4H), 2.145 (m, 2H), 2.50 (m, 1H), 3.00 (m, 2H), 3.77 (s, 2H), 4.57 (broad s, 2H, NH₂), 6.39 (d, J=8, 1H), 7.01 (d, J=7, 1H), 7.25 (m, 2H), 7.44 (t, J=8, 1H), 7.70 (s, 1H), 7.81 (m, 2H), 8.74 (s, 1H).

¹³C-NMR (δ, CDCl₃): 33.2, 42.1, 53.8, 54.3, 106.8, 110.6, 126.8, 127.0, 136.4, 137.6, 138.3, 141.7, 146.6, 153.3, 156.0, 158.2.

MS (%): 351 (parent+1, 100).

Anal. Calc'd for C₂₀H₂₂N₄S: ,C 68.54; H, 6.33; N, 15.99. Found: C, 68.21; H, 6.49; N, 15.63.

EXAMPLE 41

6-[(N-(2-Pyridyl)methyl)-4-(piperidin-4-yl)-phenyl]-pyridin-2-ylamine

Prepared from Example 13, using 2-pyridyl bromide to alkylate 6-[4-(piperidin-4-yl)-phenyl]-pyridin-2-ylamine, in 97%, mp 180–190° C. as the hydrochloride salt.

¹H-NMR (δ, CDCl₃): 1.82 (m, 4H), 2.19 (m, 2H), 2.53 (m, 1H), 3.02 (m, 2H), 3.69 (s, 2H), 4.54 (broad s, 2H, NH₂), 6.38 (d, J=8, 1H), 7.02 (d, J=7.5, 1H), 7.14 (m, 1H), 7.26 (m, 2H), 7.43 (m, 2H), 7.64 (t, J=8, 1H), 7.81 (m, 2H), 8.55 (m, 1H).

¹³C-NMR (δ, CDCl₃): 33.2, 42.2, 54.4, 64.9, 106.8, 110.6, 121.9, 123.2, 126.8, 127.0, 136.3, 137.6, 138.2, 146.8, 149.1, 156.0, 158.2, 158.7.

MS (%): 345 (parent+1, 100).

Anal. Calc'd for C₂₂H₂₄N₄.2HCl.7/4H₂O: C, 58.86; H, 6.62; N, 12.48. Found: C, 58.99; H, 6.66; N, 12.24.

EXAMPLE 42

6-[(N-(3-Pyridyl)methyl)-4-(piperidin-4-yl)-phenyl]-pyridin-2-ylamine

Prepared from Example 13, using 3-pyridyl bromide to alkylate 6-[4-(piperidin-4-yl)-phenyl]-pyridin-2-ylamine, in 86%, mp 202–215° C. as the hydrochloride salt.

¹H-NMR (δ, CDCl₃): 1.81 (m, 4H), 2.10 (m, 2H), 2.51 (m, 1H), 2.96 (m, 2H), 3.53 (s, 2H), 4.625 (broad s, 2H, NH₂), 6.38 (d, J=8, 1H), 7.01 (d, J=7.5, 1H), 7.24 (m, 3H), 7.43 (t, J=8, 1H), 7.69 (m, 1H), 7.82 (m, 2H), 8.49 (m, 1H), 8.54 (m, 1H).

¹³C-NMR (δ, CDCl₃): 33.1, 42.1, 54.1, 60.4, 106.8, 110.6, 123.3, 126.8, 127.0, 133.7, 136.8, 137.6, 138.3, 146.6, 148.4, 150.3, 155.9, 158.2.

MS (%): 345 (parent+1, 100).

Anal. Calc'd for C₂₂H₂₄N₄.3HCl.3/2H₂O: C, 54.95; H, 6.29; N, 11.65. Found: C, 54.93; H, 6.51; N, 11.31.

EXAMPLE 43

6-[(N-(2-Imidazolyl)methyl)-4-(piperidin-4-yl)-phenyl]-pyridin-2-ylamine

Prepared from Example 13, using 2-imidazolyl aldehyde to reductively aminate 6-[4-(piperidin-4-yl)-phenyl]-pyridin-2-ylamine, in 88%, mp 160–163° C.

¹H-NMR (δ, CDCl₃): 1.81 (m, 4H), 2.28 (m, 2H), 2.54 (m, 1H), 3.00 (m, 2H), 3.75 (broad s, 2H), 6.395 (d, J=8, 1H), 6.94 (m, 1H), 7.00 (d, J=7.5, 1H), 7.20 (m, 2H), 7.43 (t, J=8, 1H), 7.79 (m, 2H).

¹³C-NMR (δ, CDCl₃):32.6, 41.6, 54.0, 55.7, 107.0, 110.7, 127.0, 137.9, 138.4, 146.0, 155.9, 158.3.

MS (%): 334 (parent+1, 100).

Anal. Calc'd for C₂₀H₂₃N₅.1/2H₂CO₃: C, 67.56; H, 6.64; N, 19.22. Found: C, 67.48; H, 6.89; N, 18.91.

EXAMPLE 44

6-[(N-(4-lmidazolyl)methyl)-4-(piperidin-4-yl)-phenyl]-pyridin-2-ylamine

Prepared from Example 13, using 4-imidazolyl aldehyde to reductively aminate 6-[4-(piperidin-4-yl)-phenyl]-pyridin-2-ylamine, in 92%, mp >210° C. (dec.) as the hydrochloride salt.

¹H-NMR (δ, CDCl₃): 1.74 (m, 4H), 2.07 (m, 2H), 2.5 (m, 1H), 2.97 (m, 2H), 3.47 (s, 2H), 5.94 (broad s, 2H, NH₂), 6.39 (d, J=8, 1H), 6.90 (broad s, 1H), 7.00 (d, J=7.4, 1H), 7.27 (m, 2H), 7.42 (t, J=8, 1H), 7.56 (m, 1H), 7.88 (m, 2H).

¹³C-NMR (δ, CDCl₃): 32.8, 41.4, 53.3, 54.1, 106.7, 108.0, 126.3, 126.7, 137.3, 137.9, 146.5, 154.3, 159.5.

MS (%): 334 (parent+1, 100).

Anal. Calc'd for C₂₀H₂₃N₅.1/2H₂CO₃: C, 67.56; H, 6.64; N, 19.22. Found: C, 67.99; H, 6.72; N, 19.07.

EXAMPLE 45

6-[(N-(4-Pyridyl)methyl)-4-(piperidin-4-yl)-phenyl]-pyridin-2-ylamine

Prepared from Example 13, using 4-pyridine carboxaldehyde to reductively aminate 6-[4-(piperidin-4-yl)-phenyl]-pyridin-2-ylamine, in 74%, mp 158–163° C. as the hydrochloride salt.

¹H-NMR (δ, CDCl₃): 1.81 (m, 4H), 2.10 (m, 2H), 2.52 (m, 1H), 2.94 (m, 2H), 3.51 (s, 2H), 4.57 (broad s, 2H, NH₂), 6.39 (d, J=8, 1H), 7.02 (d, J=7, 1H), 7.28 (m, 4H), 7.43 (t, J=8, 1H), 7.83 (m, 2H), 8.52 (m, 2H).

¹³C-NMR (δ, CDCl₃): 33.4, 42.2, 54.4, 62.1, 106.9, 110.7, 123.9, 126.9, 127.1, 137.7, 138.3, 146.7, 148.1, 149.7, 156.0, 158.3.

MS (%): 345 (parent+1, 100).

Anal. Calc'd for C₂₂H₂₄N₄.5/4H₂O: C, 72.00; H, 7.28; N, 15.27. Found: C, 72.23; H, 6.97; N, 15.47.

EXAMPLE 46

6-[(N-(2-Furyl)methyl)-4-(pyrrolidin-3-yl)-phenyl]-pyridin-2-ylamine

A. Diethyl-4-[2-(2,5-dimethylpyrrolyl)-6-pyridyl] benzylidenemalonate

To a 125 mL round-bottomed flask equipped with N₂ inlet were added 3.3 g (11.96 mmol) 2-(2,5-dimethylpyrrolyl)-6-(4-(4'-formylbiphenyl-4-yl))-pyridine (Example 1B), 1.9 g (11.96 mmol) diethyl malonate, 60 mL benzene, 51 mg (0.6 mmol) piperidine, and 10 mg benzoic acid. The reaction was refluxed overnight, cooled, and poured into water and ethyl acetate. The organic layer was washed with 1N hydrochloric acid, aqueous sodium bicarbonate solution, and brine, dried over sodium sulfate, and evaporated. The residue was chromatographed on silica gel using methylene chloride/ethyl acetate to afford the product as a yellow oil, 4.32 g (86.5%).

¹H-NMR (δ, CDCl₃): 1.31 (t, J=7, 3H), 1.34 (t, J=7, 3H), 2.21 (s, 6H), 4.33 (q, J=8, 2H), 4.35 (q, J=7, 2H), 5.93 (s, 2H), 7.17 (d, J=8, 1H), 7.55 (m, 2H), 7.77 (m, 2H), 7.87 (t, J=8, 1H), 8.09 (m, 2H).

¹³C-NMR (δ, CDCl₃): 13.5, 14.0, 14.2, 61.7, 61.8, 106.1, 118.5, 120.5, 126.7, 127.2, 128.6, 129.9, 130.1, 133.7, 138.8, 140.2, 141.3, 151.8, 155.6, 164.1, 166.7.

IR (neat, cm$^{-1}$): 1727 (C=O).

MS (%): 419 (parent+1, 100).

B. Ethyl-3-[2-(2,5-dimethylpyrrolyl)-6-pyridyl]phenyl-3-cyano-propionate

To a 250 mL round-bottomed flask equipped with condenser and N$_2$ inlet were added 4.32 g (10.33 mmol) diethyl-4-[2-(2,5-dimethylpyrrolyl)-6-pyridyl] benzylidenemalonate and 100 mL ethanol. To the stirring solution was added a solution of 672 mg (10.33 mmol) potassium cyanide in 2.6 mL water, and the reaction heated at 60° C. overnight. The reaction was cooled and quenched with dilute hydrochloric acid, then taken up in ethyl acetate and washed with acid and brine, dried over sodium sulfate, and evaporated. The residue was chromatographed on silica gel using methylene chloride/ethyl acetate as eluant to afford 3.00 g (78%) of an oil.

$^1$H-NMR (δ, CDCl$_3$): 2.21 (s, 6H), 2.96 (m, 2H), 3.71 (s, 3H), 4.355 (t, J=7, 1H), 5.93 (s, 2H), 7.17 (d, J=8, 1H), 7.47 (m, 2H), 7.74 (d, J=8, 1H), 7.89 (t, J=8, 1H), 8.09 (m, 2H).

$^{13}$C-NMR (δ, CDCl$_3$): 13.5, 32.9, 39.7, 52.4, 107.1, 118.4, 113.75, 120.3, 127.8, 128.6, 135.4, 138.8, 151.8, 155.8, 169.5.

IR (neat, cm.$^{-1}$): 2244 (CN), 1739 (C=O).

MS (%): 374 (parent+1, 100).

C. 2-(2,5-Dimethylpyrrolyl)-6-[4-(2-oxo-pyrrolidin-3-yl)-phenyl]-pyridine

To a 125 mL round-bottomed flask equipped with condenser and N$_2$ inlet were added 2.84 g (7.61 mmol) ethyl-3-[2-(2,5-dimethylpyrrolyl)-6-pyridyl]phenyl-3-cyano-propionate, 50 mL ethanol, and 1 mL concentrated hydrochloric acid. The solution was heated as 700 mg 10% palladium-on-carbon and 2.4 g (38.07 mmol) ammonium formate were added, and the reaction heated at 80° C. for 4.75 hours, with additional catalyst and ammonium formate at 1 hour intervals. The reaction was cooled and filtered through Celite, and the filtrate evaporated. The residue was taken up in ethyl acetate, washed with aqueous sodium hydroxide, dried over sodium sulfate, and evaporated. The residue was taken up in 50 mL dry toluene, treated with 5 mL triethylamine, and heated at reflux for 1 hour. The reaction was then cooled, washed with dilute aqueous hydrochloric acid and brine, dried over sodium sulfate, and evaporated. The residue was chromatographed on silica gel using methylene chloride/methanol as eluant to afford 204.5 mg (8.1%) of an oil.

$^1$H-NMR (δ, CDCl$_3$): 2.21 (s, 6H), 2.64 (AB, J=8.5, 17, Dn=94, 2H), 3.43 (dd, J=7,9, 1H), 3.73 (m, 1H), 3.80 (m, 1H), 5.92 (s, 2H), 7.02 (bs, 1H), 7.13 (d, J=8, 1H), 7.34 (m, 2H), 7.72 (d, J=8, 1H), 7.86 (t, J=8, 1H), 8.04 (m, 2H).

$^{13}$C-NMR (δ, CDCl$_3$): 13.5, 38.0, 40.0, 49.5, 107.0, 118.2, 119.9, 127.2, 127.4, 128.7, 137.3, 138.7, 143.5, 151.7, 156.3, 177.8.

IR (neat, cm.$^{-1}$): 1708 and 1685 (C=O).

MS (%): 332 (parent+1, 100).

D. 2-(2,5-Dimethylpyrrolyl)-6-[4-(pyrrolidin-3-yl)-phenyl]-pyridine

To a 125 mL round-bottomed flask equipped with condenser and N$_2$ inlet were added 230 mg (1.73 mmol) aluminum chloride and 8 mL dry tetrahydrofuran. The solution was cooled to 0° C., and 4.04 mL (4.04 mmol) of a 1.0 M solution was lithium aluminum hydride in tetrahydrofuran was added. The reaction was stirred 20 minutes at room temperature, and cooled to −70° C. The reaction was treated with a solution of 191 mg (0.577 mmol) 2-(2,5-dimethylpyrrolyl)-6-[4-(pyrrolidin-3-yl)-phenyl]-pyridine in 2 mL dry tetrahydrofuran, and stirred 1 hour at −70° C. and 14 hours at room temperature. The reaction was carefully quenched with dilute aqueous hydrochloric acid, then taken up in methylene chloride and aqueous sodium hydroxide solution, and the combined organic layer washed with water, dried over sodium sulfate, and evaporated to afford 145 mg (79%) of an oil.

$^1$H-NMR (δ, CDCl$_3$): 1.90 (m, 1H), 2.21 (s, 6H), 2.27 (m, 1H), 2.89 (dd, J=8,10, 1H), 3.11 (m, 1H), 3.19 (m, 1H), 3.28 (t, J=8, 1H), 3.40 (dd, J=8,10, 1H), 3.5 (bs, 1H), 5.92 (s, 2H), 7.10 (d, J=8, H), 7.33 (m, 2H), 7.70 (d, J=8, 1H), 7.83 (t, J=8, 1H), 8.00 (m, 2H).

$^{13}$C-NMR (δ, CDCl$_3$): 13.5, 34.4, 45.3, 47.2, 54.8, 106.9, 118.1, 119.7, 125.5, 127.1, 127.2, 127.4, 127.6, 128.6, 136.5, 138.6, 145.3, 151.6, 156.6.

MS (%): 318 (parent+1, 100).

E. 2-(2,5-Dimethylpyrrolyl)-6-[(N-(2-furyl)methyl)-4-(pyrrolidin-3-yl)-phenyl]-pyridine Prepared using the procedure in Example 43 to carry out the reductive amination with furfural, in 65% yield as an oil.

$^1$H-NMR (δ, CDCl$_3$): 1.92 (m, 1H), 2.21 (s, 6H), 2.36 (m, 1H), 2.59 (t, J=9, 1H), 2.78 (m, 1H), 2.97 (m, 1H), 3.18 (t, J=9, 1H), 3.44 (m, 1H), 3.75 (Ab$_q$, J=14, Dn=19, 2H), 5.92 (s, 2H), 6.24 (d, J=3, 1H), 6.32 (dd, J=2,3, 1H), 7.10 (d, J=8, 1H), 7.34 (m, 2H), 7.38 (d, J=2, 1H), 7.70 (d, J=8, 1H), 7.83 (t, J=8, 1H), 7.99 (m, 2H).

$^{13}$C-NMR (δ, CDCl$_3$): 13.4, 33.0, 43.1, 51.7, 54.1, 61.4, 106.8, 108.2, 110.1, 118.0, 119.6, 126.9, 127.1, 127.3, 128.7, 130.8, 136.3, 138.5, 142.1, 146.05, 151.5, 152.0, 156.6.

MS (%): 398 (parent+1, 100).

F. 6-[(N-(2-Furyl)methyl)-4-(pyrrolidin-3-yl)-phenyl]-pyridin-2-ylamine

Prepared as in Example 11D, in 77% yield, mp 60–70° C. as the hydrochloride salt.

$^1$H-NMR (δ, CDCl$_3$): 1.90 (m, 1H), 2.34 (m, 1H), 2.51 (t, J=9, 1H), 2.70 (m, 1H), 2.93 (m, 1H), 3.13 (t, J=9, 1H), 3.65 (m, 1H), 3.69 (Ab$_q$, J=14, Dn=21, 2H), 4.55 (bs, 2H, NH$_2$), 6.19 (d, J=3, 1H), 6.30 (dd, J=2,3, 1H), 6.40 (d, J=8, 1H), 7.02 (d, J=7, 1H), 7.29 (m, 2H), 7.36 (m, 1H), 7.45 (t, J=8, 1H), 7.81 (m, 2H).

$^{13}$C-NMR (δ, CDCl$_3$): 33.1, 43.1, 52.0, 54.2, 61.75, 106.8, 107.7, 110.0, 110.6, 126.8, 127.1, 127.4, 167.6, 138.3, 141.9, 145.5, 152.6, 155.9, 158.2.

MS (%): 320 (parent+1, 100).

Anal. Calc'd for $C_{20}H_{21}N_3O.2HCl.5/3H_2O$: C, 56.88; H, 6.28; N, 9.95. Found: C, 56.67; H, 6.11; N, 10.15.

EXAMPLE 47

6-[(N-(2-Methyl)propyl)-4-(pyrrolidin-3-yl)-phenyl]-pyridin-2-ylamine

Prepared as in Example 46, using isobutyraldehyde, with a 73% yield in the final deblocking step to afford the product as a solid, mp 55–70° C.

$^1$H-NMR (δ, CDCl$_3$): 0.93 (d, J=6.5, 6H), 1.76 (m, 1H), 1.87 (m, 1H), 2.2–2.4 (m, 3H), 2.49 (dd, J=8,9, 1H), 2.64 (m, 1H), 2.76 (m, 1H), 2.98 (t, J=9, 1H), 3.37 (h, J=7, 1H), 4.56 (bs, 2H, NH$_2$), 6.40 (d, J=8, 1H), 7.03 (d, J=7.5, 1H), 7.32 (m, 2H), 7.45 (t, J=8, 1H), 7.81 (m, 2H).

$^{13}$C-NMR (δ, CDCl$_3$): 21.0, 27.4, 33.2, 43.0, 54.9, 62.4, 64.9, 106.8, 110.7, 126.8, 127.5, 137.5, 138.3, 146.4, 156.0, 158.2.

MS (%): 296 (parent+1, 100).

Anal. Calc'd for $C_{19}H_{25}N_3 \cdot 2HCl \cdot 2H_2O$: C, 56.43; H, 7.73; N, 10.39. Found: C, 56.13; H, 7.52; N, 10.40.

EXAMPLE 48

8-[4-(6-Amino-pyridin-2-yl)-phenyl]-3-isobutyl-3-aza-bicyclo[3.2.1]octan-8-ol A. 8-[4-(6-(2,5-Dimethylpyrrolyl)-pyridin-2-yl)-phenyl]-3-benzyl-3-aza-bicyclo[3.2.1]octan-8-ol To a 125 mL 3-necked round-bottomed flask equipped with septum and $N_2$ inlet were added 1.86 g (5.70 mmol) 6-bromo-2-(2,5-dimethylpyrrolyl)-pyridine and 40 mL dry tetrahydrofuran. The solution was cooled to −60° C., and 2.73 mL (6.84 mmol) of a 2.5M solution of butyl lithium in hexane was added dropwise and the solution stirred 10 min at −60° C. Then a solution of 1.47 g (6.84 mmol) 3-benzyl-3-aza-bicyclo[3.2.1]octan-8-one in 15 mL dry tetrahydrofuran was added dropwise, and the reaction stirred at −60° C. for 10 minutes, and then at room temperature for 3 hours. The reaction was quenched with aqueous ammonium chloride solution and taken up in ethyl acetate. The organic layer was separated and washed with more aqueous ammonium chloride solution and brine, dried over sodium sulfate, and evaporated. The residue was chromatographed on silica gel using methanol and methylene chloride to afford 413 mg (16%) of a yellow oil which solidified, mp 58–68° C.

$^1$H-NMR (δ, $CDCl_3$): 1.45 (m, 2H), 1.84 (m, 2H), 2.22 (s, 6H), 2.46 (bs, 2H), 2.66 (m, 2H), 2.92 (m, 2H), 3.64 (s, 2H), 5.94 (s, 2H), 7.14 (d, J=8, 1H), 7.2–7.4 (m, 5H), 7.959 (m, 2H), 7.74 (d, J=8, 1H), 7.865 (t, J=8, 1H), 8.065 (m, 2H).

$^{13}$C-NMR (δ, $CDCl_3$): 13.5, 25.5, 41.8, 54.0, 61.8, 78.9, 107.0, 118.3, 120.0, 125.9, 126.8, 127.1, 128.2, 128.7, 137.6, 138.6, 151.7, 156.4.

MS (%): 464 (parent+1, 100).

B. 8-[4-(6-(2,5-Dimethylpyrrolyl)-pyridin-2-y1)-phenyl]-3-aza-bicyclo[3.2.1]octan-8-ol Prepared as in Example 13C in 73% yield as a solid, mp 185–190° C.

$^1$H-NMR (δ, $CDCl_3$): 1.52 (m, 4H), 2.19 (s, 6H), 2.35 (m, 2H), 2.53 (m, 2H), 3.48 (m, 2H), 5.91 (s, 2H), 7.12 (d, J=8, 1H), 7.55 (m, 2H), 7.72 (d, J=8, 1H), 7.85 (t, J=8, 1H), 8.04 (m, 2H).

$^{13}$C-NMR (δ, $CDCl_3$): 13.5, 24.7, 42.0, 47.1, 78.9, 107.0, 118.3, 119.9, 125.6, 127.1, 128.6, 137.5, 138.6, 147.1, 151.7, 156.4.

MS (%): 374 (parent+1, 100).

Anal. Calc'd for $C_{24}H_{27}N_3O \cdot 1/4(C_4H_8O_3)$: C, 75.92; H, 7.39; N, 10.62. Found: C, 76.13; H, 7.37; N, 10.33.

C. 8-[4-(6-amino-pyridin-2-yl)-phenyl]-3-aza-bicyclo[3.2.1]octan-8-ol

Prepared as in Example 11 D in 84% yield as a solid, mp 108–120° C.

$^1$H-NMR (δ, $CDCl_3$): 1.46 (m, 4H), 2.29 (m, 2H), 2.47 (m, 2H), 3.39 (m, 2H), 4.635 (bs, 2H, $NH_2$), 6.365 (d, J=8, 1H), 6.94 (d, J=7.5, 1H), 7.41 (t, J=8, 1H), 7.44 (m, 2H), 7.75 (m, 2H).

$^{13}$C-NMR (δ, $CDCl_3$): 24.4, 41.5, 46.7, 78.3, 107.3, 110.8, 125.3, 125.5, 126.9, 138.4, 138.6, 145.8, 155.6, 158.4.

MS (%): 296 (parent+1, 100).

HRMS Calc'd for $C_{18}H_{21}N_3O$: 286.1763. Found: 286.1776.

D. 8-[4-(6-Amino-pyridin-2-yl)-phenyl]-3-isobutyl-3-aza-bicyclo[3.2.1]octan-8-ol Prepared as in Example 47 in 27% yield, mp 167–200° C.

$^1$H-NMR (δ, $CDCl_3$): 0.90 (d, J=6, 6H), 1.39 (m, 2H), 1.8 (broad m, 3H), 2.2 (broad m, 2H), 2.425 (bs, 2H), 2.64 (m, 2H), 2.83 (m, 2H), 4.51 (bs, 2H, $NH_2$), 6.42 (d, J=8, 1H), 7.04 (d, J=7.5, 1H), 7.465 (t, J=8, 1H), 7.52 (m, 2H), 7.86 (m, 2H).

$^{13}$C-NMR (δ, $CDCl_3$): 20.8, 25.15, 25.6, 41.5, 54.4, 65.6, 78.45, 107.4, 111.1, 125.6, 127.0, 138.6, 138.8, 155.7, 158.4.

MS (%): 352 (parent+1, 100).

Anal. Calc'd for $C_{22}H_{29}N_3O \cdot 2HCl \cdot H_2O$: C, 57.64; H, 7.26; N, 9.17. Found: C, 57.60; H, 7.34; N, 8.84.

EXAMPLE 49

8-[4-(6-Amino-pyridin-2-yl)-phenyl]-3-furan-2-ylmethyl-3-aza-bicyclo[3.2.1]octan-8-ol Prepared as in Example 48, using furfural, with a 33% yield in the final deblocking step to afford the product as a solid, mp 187–202° C.

$^1$H-NMR (δ, $CDCl_3$): 1.41 (m, 2H), 1.78 (m, 2H), 2.435 (m, 2H), 2.65 (m, 2H), 3.00 (m, 2H), 3.68 (s, 2H), 4.52 (bs, 2H, $NH_2$), 6.24 (d, J=3, 1H), 6.32 (dd, J=2,3, 1H), 6.415 (d, J=8, 1H), 7.03 (d, J=7.5, 1H), 7.37 (d, J=2, 1H), 7.46 (t, J=8, 1H), 7.50 (m, 2H), 7.84 (m, 2H).

$^{13}$C-NMR (δ, $CDCl_3$): 25.1, 41.5, 53.6, 53.8, 78.5, 107.3, 108.6, 110.1, 111.0, 125.6, 127.0 138.4, 139.0, 141.9, 145.1, 155.6, 158.3.

MS (%): 376 (parent+1, 100).

Anal. Calc'd for $C_{23}H_{25}N_3O_2 \cdot 2HCl \cdot H_2O$: C, 59.23; H, 6.27; N, 9.01. Found: C, 59.17; H, 6.50; N, 8.71.

EXAMPLE 50

8-[4-(6-Amino-pyridin-2-yl)-phenyl]-3-benzyl-3-aza-bicyclo[3.2.1]octan-8-ol

Prepared as in Example 46, deblocking after step A. to afford the product as a solid, mp 185–200° C. (dec.).

$^1$H-NMR (δ, $CDCl_3$): 1.41 (m, 2H), 1.79 (m, 2H), 2.41 (bs, 2H), 2.63 (m, 2H), 2.91 (m, 2H), 3.62 (s, 2H), 4.58 (bs, 2H, NH2), 6.41 (d, J=8, 1H), 7.02 (d, J=7.5, 1H), 7.23 (m, 1H), 7.31 (m, 2H), 7.37 (m, 2H), 7.45 (t, J =8, 1H), 7.51 (m, 2H), 7.83 (m, 2H).

$^{13}$C-NMR (δ, $CDCl_3$): 25.4, 41.7, 54.0, 61.8, 78.7, 107.3, 111.0, 125.6, 126.8, 127.0, 128.2, 128.8, 138.4, 138.9, 145.4, 155.7, 158.3.

MS (%): 386 (parent+1, 100).

Anal. Calc'd for $C_{25}H_{27}N_3O \cdot 1/4CH_2Cl_2 \cdot 1/2(C_4H_{10}O)$: C, 63.34; H, 6.73; N, 8.13. Found: C, 63.11; H, 6.44; N, 8.12.

What is claimed is:

1. A compound of the formula

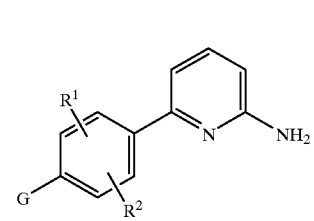

(I)

wherein $R^1$ and $R^2$ are selected, independently, from hydrogen, hydroxy, methyl and methoxy;

G is selected from a group of the formula

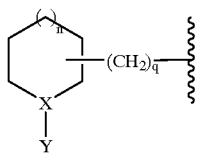
(A)

n is one;
Y is hydrogen, $(C_1-C_6)$alkyl, or aralkyl, wherein the aryl moiety of said aralkyl is phenyl, naphthyl, isoxazolyl, methylenedioxybenzyl, imidazolyl, pyridyl, furyl, thiazolyl, or isothiazolyl, and the alkyl moiety is straight or branched and contains from 1 to 6 carbon atoms, and wherein said $(C_1-C_6)$alkyl and the aryl moiety of said aralkyl may be substituted with from zero to three substituents, that are selected, independently, from phenyl, —C(O)NH$_2$, —C(O)phenyl, chloro, fluoro, bromo, iodo, nitro, hydroxy, cyano, amino, $(C_1-C_4)$alkoxy and $(C_1-C_4)$ alkylamino;
X is N; and
q is zero, one or two;
or a pharmaceutically acceptable salt of such compound.

2. A compound according to claim 1, wherein G is a group of the formula

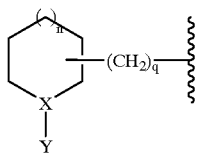
(A)

wherein n is one;
Y is $(C_1-C_6)$alkyl or aralkyl, wherein the aryl moiety of said aralkyl is phenyl or naphthyl and the alkyl moiety is straight or branched and contains from 1 to 6 carbon atoms, and wherein said $(C_1-C_6)$alkyl and the aryl moiety of said aralkyl may be substituted with from zero to three substituents, that are selected, independently, from chloro, fluoro, bromo, iodo, nitro, hydroxy, cyano, amino, $(C_1-C_4)$alkoxy and $(C_1-C_4)$ alkylamino;
X is N; and
q is zero, one or two;
or a pharmaceutically acceptable salt of such compound.

3. A compound according to claim 1, wherein q is zero or one.

4. A compound according to claim 1 selected from the group consisting of

6-[(N-(5-isothiazolyl)methyl)-4-(piperidin-4-yl)-phenyl]-pyridin-2-ylamine;
6-[(N-(5-thiazolyl)methyl)-4-(piperidin-4-yl)-phenyl]-pyridin-2-ylamine;
and pharmaceutically acceptable salts thereof.

5. A pharmaceutical composition for treating or preventing a condition selected from the group consisting of depression, migraine, inflammatory diseases, stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addictions, emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, Parkinson's disease, glaucoma, macular degeneration, diabetic neuropathy, diabetic nephropathy and cancer in a mammal, comprising an amount of a compound according to claim 1 that is effective in treating such condition and a pharmaceutically acceptable carrier.

6. A method of inhibiting NOS in a mammal, comprising administering to said mammal a NOS inhibiting effective amount of a compound according to claim 5.

7. A method of inhibiting iNOS or nNOS in a mammal, comprising administering to said mammal a NOS inhibiting effective amount of a compound according to claim 1.

8. A method of treating a condition selected from the group consisting of migraine, inflammatory diseases, stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addictions, emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, Parkinson's disease, glaucoma, macular degeneration, diabetic neuropathy, diabetic nephropathy and cancer in a mammal, comprising administering to said mammal an amount of a compound according to claim 1, that is effective in treating such condition.

9. A method of treating depression in a mammal comprising administering to said mammal an amount of a compound according to claim 1 that is effective in treating depression.

* * * * *